(12) United States Patent
Girardeau-Montaut et al.

(10) Patent No.: US 12,369,981 B2
(45) Date of Patent: Jul. 29, 2025

(54) SYSTEMS AND METHODS FOR BONE MODEL REGISTRATION WITH ADAPTIVE SOFT TISSUE THICKNESS

(71) Applicant: DEPUY IRELAND UNLIMITED COMPANY, Ringaskiddy (IE)

(72) Inventors: Daniel Girardeau-Montaut, Grenoble (FR); Nicolas Demanget, Cambridge, MA (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 228 days.

(21) Appl. No.: 18/106,892

(22) Filed: Feb. 7, 2023

(65) Prior Publication Data

US 2024/0261027 A1 Aug. 8, 2024

(51) Int. Cl.
*A61B 34/10* (2016.01)
*G06T 7/33* (2017.01)
(Continued)

(52) U.S. Cl.
CPC ............... *A61B 34/10* (2016.02); *G06T 7/33* (2017.01); *G06T 7/73* (2017.01); *G06T 19/20* (2013.01);
(Continued)

(58) Field of Classification Search
CPC .............. A61B 34/10; A61B 2034/105; A61B 2034/2055; A61B 2034/2068;
(Continued)

(56) References Cited

U.S. PATENT DOCUMENTS 3,847,157 A 11/1974 Caillouette et al.
4,054,881 A 10/1977 Raab
(Continued)

FOREIGN PATENT DOCUMENTS

CA 2517250 A1 9/2004
CN 113100939 A * 7/2021 ............. A61B 34/10
(Continued)

OTHER PUBLICATIONS

Gao, Nuo, Detecting Human Head Conductivity Distribution Using One Component Magnetic Flux Density, Sep. 2005, IEEE, pp. 1537-1539.
(Continued)

*Primary Examiner* — Ryan R Yang
(74) *Attorney, Agent, or Firm* — Barnes & Thornburg LLP

(57) ABSTRACT

Systems and methods for planning and assisting orthopaedic surgical procedures include a computing device and a robotic surgical device. The computing device defines a surgical coordinate system relative to a bone of a patient and captures a plurality of point positions in the surgical coordinate system. The plurality of point positions includes a first point position representing a location on a soft tissue surface covering a portion of the patient's bone. The computing device identifies an estimated soft tissue thickness value for each of the plurality of point positions and registers a three-dimensional model of the patient's bone in the surgical coordinate system based on the plurality of point positions and the estimated soft tissue thickness values. The computer system may control the robotic surgical device according to the registered bone model.

20 Claims, 13 Drawing Sheets

(51) Int. Cl.
   *G06T 7/73*      (2017.01)
   *G06T 19/20*     (2011.01)
   *A61B 34/20*     (2016.01)
   *A61B 90/00*     (2016.01)

(52) U.S. Cl.
   CPC . *A61B 2034/105* (2016.02); *A61B 2034/2055* (2016.02); *A61B 2034/2068* (2016.02); *A61B 2090/364* (2016.02); *G06T 2207/10028* (2013.01); *G06T 2207/30008* (2013.01); *G06T 2219/2004* (2013.01)

(58) Field of Classification Search
   CPC ....... A61B 2090/364; G06T 7/33; G06T 7/73; G06T 19/20; G06T 2207/10028; G06T 2207/30008; G06T 2219/2004
   See application file for complete search history.

(56) References Cited

U.S. PATENT DOCUMENTS

| | | |
|---|---|---|
| 4,063,561 A | 12/1977 | Mckenna |
| 4,173,228 A | 11/1979 | Childress et al. |
| 4,244,362 A | 1/1981 | Anderson |
| 4,328,548 A | 5/1982 | Crow et al. |
| 4,396,885 A | 8/1983 | Constant |
| 4,422,041 A | 12/1983 | Lienau |
| 4,431,005 A | 2/1984 | Mccormick |
| 4,622,644 A | 11/1986 | Hansen |
| 4,652,820 A | 3/1987 | Maresca |
| 4,661,773 A | 4/1987 | Kawakita et al. |
| 4,677,380 A | 6/1987 | Popovic et al. |
| 4,700,211 A | 10/1987 | Popovic et al. |
| 4,710,708 A | 12/1987 | Rorden et al. |
| 4,790,809 A | 12/1988 | Kuntz |
| 4,791,934 A | 12/1988 | Brunnett |
| 4,809,713 A | 3/1989 | Grayzel |
| 4,829,250 A | 5/1989 | Rotier |
| 4,849,692 A | 7/1989 | Blood |
| 4,905,698 A | 3/1990 | Strohl, Jr. et al. |
| 4,943,770 A | 7/1990 | Ashley-Rollman et al. |
| 5,023,725 A | 6/1991 | Mccutchen |
| 5,099,845 A | 3/1992 | Besz et al. |
| 5,113,136 A | 5/1992 | Hayashi et al. |
| 5,206,589 A | 4/1993 | Kado et al. |
| 5,211,165 A | 5/1993 | Dumoulin et al. |
| 5,230,623 A | 7/1993 | Guthrie et al. |
| 5,251,635 A | 10/1993 | Dumoulin et al. |
| 5,253,647 A | 10/1993 | Noguchi et al. |
| 5,255,680 A | 10/1993 | Darrow et al. |
| 5,257,636 A | 11/1993 | White |
| 5,265,610 A | 11/1993 | Darrow et al. |
| 5,273,025 A | 12/1993 | Sakiyama et al. |
| 5,377,678 A | 1/1995 | Dumoulin et al. |
| 5,383,454 A | 1/1995 | Bucholz |
| 5,389,101 A | 2/1995 | Heilbrun et al. |
| 5,425,382 A | 6/1995 | Golden et al. |
| 5,438,990 A | 8/1995 | Wahlstrand et al. |
| 5,456,718 A | 10/1995 | Szymaitis |
| 5,558,091 A | 9/1996 | Acker et al. |
| 5,622,169 A | 4/1997 | Golden et al. |
| 5,631,557 A | 5/1997 | Davidson |
| 5,648,719 A | 7/1997 | Christensen et al. |
| 5,694,040 A | 12/1997 | Plagens |
| 5,711,299 A | 1/1998 | Manwaring et al. |
| 5,713,946 A | 2/1998 | Ben-Haim |
| 5,729,129 A | 3/1998 | Acker |
| 5,731,996 A | 3/1998 | Gilbert |
| 5,752,513 A | 5/1998 | Acker et al. |
| 5,761,332 A | 6/1998 | Wischmann et al. |
| 5,762,064 A | 6/1998 | Polvani |
| 5,775,322 A | 7/1998 | Silverstein et al. |
| 5,799,099 A | 8/1998 | Wang et al. |
| 5,833,608 A | 11/1998 | Acker |
| 5,834,709 A | 11/1998 | Blonder et al. |
| 5,842,986 A | 12/1998 | Avrin et al. |
| 5,879,297 A | 3/1999 | Haynor et al. |
| 5,902,238 A | 5/1999 | Golden et al. |
| 5,913,820 A | 6/1999 | Bladen et al. |
| 5,942,895 A | 8/1999 | Popovic et al. |
| 5,944,022 A | 8/1999 | Nardella et al. |
| 5,944,023 A | 8/1999 | Johnson et al. |
| 5,967,980 A | 10/1999 | Ferre et al. |
| 5,983,126 A | 11/1999 | Wittkampf |
| 5,987,349 A | 11/1999 | Schulz |
| 6,015,414 A | 1/2000 | Werp et al. |
| 6,052,610 A | 4/2000 | Koch |
| 6,059,718 A | 5/2000 | Taniguchi et al. |
| 6,064,905 A | 5/2000 | Webster, Jr. et al. |
| 6,073,043 A | 6/2000 | Schneider |
| 6,076,007 A | 6/2000 | England et al. |
| 6,104,944 A | 8/2000 | Martinelli |
| 6,122,538 A | 9/2000 | Sliwa, Jr. et al. |
| 6,129,668 A | 10/2000 | Haynor et al. |
| 6,146,390 A | 11/2000 | Heilbrun et al. |
| 6,147,480 A | 11/2000 | Osadchy et al. |
| 6,148,823 A | 11/2000 | Hastings |
| 6,157,853 A | 12/2000 | Blume et al. |
| 6,161,032 A | 12/2000 | Acker |
| 6,165,181 A | 12/2000 | Heilbrun et al. |
| 6,167,145 A | 12/2000 | Foley et al. |
| 6,167,292 A | 12/2000 | Badano et al. |
| 6,173,715 B1 | 1/2001 | Sinanan et al. |
| 6,177,792 B1 | 1/2001 | Govari et al. |
| 6,184,679 B1 | 2/2001 | Popovic et al. |
| 6,185,448 B1 | 2/2001 | Borovsky |
| 6,198,963 B1 | 3/2001 | Haim et al. |
| 6,201,387 B1 | 3/2001 | Govari |
| 6,203,493 B1 | 3/2001 | Ben-Haim |
| 6,210,362 B1 | 4/2001 | Ponzi |
| 6,211,666 B1 | 4/2001 | Acker |
| 6,212,419 B1 | 4/2001 | Blume et al. |
| 6,216,028 B1 | 4/2001 | Haynor et al. |
| 6,230,038 B1 | 5/2001 | von Gutfeld et al. |
| 6,235,038 B1 | 5/2001 | Unter et al. |
| 6,236,875 B1 | 5/2001 | Bucholz et al. |
| 6,241,671 B1 | 6/2001 | Ritter et al. |
| 6,246,900 B1 | 6/2001 | Cosman et al. |
| 6,263,230 B1 | 7/2001 | Haynor et al. |
| 6,285,902 B1 | 9/2001 | Kienzle, III et al. |
| 6,292,678 B1 | 9/2001 | Hall et al. |
| 6,304,768 B1 | 10/2001 | Blume et al. |
| 6,304,769 B1 | 10/2001 | Arenson et al. |
| 6,311,082 B1 | 10/2001 | Creighton et al. |
| 6,314,310 B1 | 11/2001 | Ben-Haim et al. |
| 6,321,109 B2 | 11/2001 | Ben-Haim et al. |
| 6,332,089 B1 | 12/2001 | Acker et al. |
| 6,337,708 B1 | 1/2002 | Furlan et al. |
| 6,341,231 B1 | 1/2002 | Ferre et al. |
| 6,347,240 B1 | 2/2002 | Foley et al. |
| 6,366,799 B1 | 4/2002 | Acker et al. |
| 6,370,224 B1 | 4/2002 | Simon et al. |
| 6,373,240 B1 | 4/2002 | Govari |
| 6,374,134 B1 | 4/2002 | Bladen et al. |
| 6,381,485 B1 | 4/2002 | Hunter et al. |
| 6,385,472 B1 | 5/2002 | Hall et al. |
| 6,401,723 B1 | 6/2002 | Garibaldi et al. |
| 6,402,762 B2 | 6/2002 | Hunter et al. |
| 6,405,072 B1 | 6/2002 | Cosman |
| 6,418,335 B2 | 7/2002 | Avrin et al. |
| 6,424,856 B1 | 7/2002 | Vilsmeier et al. |
| 6,427,079 B1 | 7/2002 | Schneider et al. |
| 6,427,314 B1 | 8/2002 | Acker |
| 6,428,551 B1 | 8/2002 | Hall et al. |
| 6,430,434 B1 | 8/2002 | Mittelstadt |
| 6,434,415 B1 | 8/2002 | Foley et al. |
| 6,442,416 B1 | 8/2002 | Schultz |
| 6,445,943 B1 | 9/2002 | Ferre et al. |
| 6,459,924 B1 | 10/2002 | Creighton et al. |
| 6,474,341 B1 | 11/2002 | Hunter et al. |
| 6,475,223 B1 | 11/2002 | Werp et al. |
| 6,490,467 B1 | 12/2002 | Bucholz et al. |
| 6,491,702 B2 | 12/2002 | Heilbrun et al. |
| 6,493,573 B1 | 12/2002 | Martinelli et al. |

(56) References Cited

U.S. PATENT DOCUMENTS

| | | |
|---|---|---|
| 6,496,713 B2 | 12/2002 | Avrin et al. |
| 6,498,477 B1 | 12/2002 | Govari et al. |
| 6,499,488 B1 | 12/2002 | Hunter et al. |
| 6,505,062 B1 | 1/2003 | Ritter et al. |
| 6,507,751 B2 | 1/2003 | Blume et al. |
| 6,511,417 B1 | 1/2003 | Miyagi et al. |
| 6,516,212 B1 | 2/2003 | Bladen et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,529,761 B2 | 3/2003 | Creighton et al. |
| 6,535,756 B1 | 3/2003 | Simon et al. |
| 6,537,196 B1 | 3/2003 | Creighton et al. |
| 6,539,327 B1 | 3/2003 | Dassot et al. |
| 6,545,462 B2 | 4/2003 | Schott et al. |
| 6,546,279 B1 | 4/2003 | Bova et al. |
| 6,553,326 B1 | 4/2003 | Kirsch et al. |
| 6,574,492 B1 | 6/2003 | Ben-Haim et al. |
| 6,574,498 B1 | 6/2003 | Gilboa |
| 6,580,938 B1 | 6/2003 | Acker |
| 6,584,174 B2 | 6/2003 | Schubert et al. |
| 6,593,884 B1 | 7/2003 | Gilboa et al. |
| 6,611,141 B1 | 8/2003 | Schulz et al. |
| 6,611,282 B1 | 8/2003 | Trubko et al. |
| 6,618,612 B1 | 9/2003 | Acker et al. |
| 6,622,098 B2 | 9/2003 | Updegrove |
| 6,625,563 B2 | 9/2003 | Kirsch et al. |
| 6,633,773 B1 | 10/2003 | Reisfeld |
| 6,640,127 B1 | 10/2003 | Kosaka et al. |
| 6,662,034 B2 | 12/2003 | Segner et al. |
| 6,662,036 B2 | 12/2003 | Cosman |
| 6,687,531 B1 | 2/2004 | Ferre et al. |
| 6,690,963 B2 | 2/2004 | Ben-Haim et al. |
| 6,701,174 B1 | 3/2004 | Krause et al. |
| 6,701,179 B1 | 3/2004 | Martinelli et al. |
| 6,702,804 B1 | 3/2004 | Ritter et al. |
| 6,725,080 B2 | 4/2004 | Melkent et al. |
| 6,733,511 B2 | 5/2004 | Hall et al. |
| 6,738,656 B1 | 5/2004 | Ferre et al. |
| 6,740,103 B2 | 5/2004 | Hall et al. |
| 6,755,816 B2 | 6/2004 | Ritter et al. |
| 6,757,557 B1 | 6/2004 | Bladen et al. |
| 6,772,002 B2 | 8/2004 | Schmidt et al. |
| 6,786,219 B2 | 9/2004 | Garibaldi et al. |
| 6,817,364 B2 | 11/2004 | Garibaldi et al. |
| 6,827,723 B2 | 12/2004 | Carson |
| 6,834,201 B2 | 12/2004 | Gillies et al. |
| 6,892,090 B2 | 5/2005 | Verard et al. |
| 6,895,267 B2 | 5/2005 | Panescu et al. |
| 6,902,528 B1 | 6/2005 | Garibaldi et al. |
| 6,911,026 B1 | 6/2005 | Hall et al. |
| 6,920,347 B2 | 7/2005 | Simon et al. |
| 6,925,339 B2 | 8/2005 | Grimm et al. |
| 6,934,575 B2 | 8/2005 | Ferre et al. |
| 6,937,906 B2 | 8/2005 | Terry et al. |
| 6,947,786 B2 | 9/2005 | Simon et al. |
| 6,968,846 B2 | 11/2005 | Viswanathan |
| 6,977,504 B2 | 12/2005 | Wright et al. |
| 6,977,594 B2 | 12/2005 | Hudman et al. |
| 6,978,166 B2 | 12/2005 | Foley et al. |
| 7,525,309 B2 | 4/2009 | Sherman et al. |
| 8,594,395 B2 | 11/2013 | Roose et al. |
| 10,198,968 B2 | 2/2019 | Imhauser et al. |
| 10,987,176 B2* | 4/2021 | Poltaretskyi ............ G16H 50/30 |
| 11,179,165 B2* | 11/2021 | Schoenefeld .......... A61B 17/17 |
| 11,931,107 B1* | 3/2024 | Janna .................... A61B 90/36 |
| 2001/0011175 A1 | 8/2001 | Hunter et al. |
| 2001/0039421 A1 | 11/2001 | Heilbrun et al. |
| 2002/0016542 A1 | 2/2002 | Blume et al. |
| 2002/0019644 A1 | 2/2002 | Hastings et al. |
| 2002/0021124 A1 | 2/2002 | Schott et al. |
| 2002/0030483 A1 | 3/2002 | Gilboa |
| 2002/0032380 A1 | 3/2002 | Acker et al. |
| 2002/0087062 A1 | 7/2002 | Schmidt et al. |
| 2002/0100486 A1 | 8/2002 | Creighton, IV et al. |
| 2002/0116043 A1 | 8/2002 | Garibaldi et al. |
| 2002/0183610 A1 | 12/2002 | Foley et al. |
| 2002/0188194 A1 | 12/2002 | Cosman |
| 2003/0006759 A1 | 1/2003 | Govari |
| 2003/0023161 A1 | 1/2003 | Govari et al. |
| 2003/0040671 A1 | 2/2003 | Somogyi et al. |
| 2003/0088179 A1 | 5/2003 | Seeley et al. |
| 2003/0090265 A1 | 5/2003 | Wan et al. |
| 2003/0153827 A1 | 8/2003 | Ritter et al. |
| 2003/0179856 A1 | 9/2003 | Mitschke et al. |
| 2004/0046558 A1 | 3/2004 | Matsumoto |
| 2004/0073279 A1 | 4/2004 | Malackowski et al. |
| 2004/0207396 A1 | 10/2004 | Xiao |
| 2004/0215071 A1 | 10/2004 | Frank et al. |
| 2004/0232913 A1 | 11/2004 | Schott et al. |
| 2004/0249262 A1 | 12/2004 | Werp et al. |
| 2004/0260172 A1 | 12/2004 | Ritter et al. |
| 2005/0010301 A1 | 1/2005 | Disilvestro et al. |
| 2005/0015003 A1 | 1/2005 | Lachner et al. |
| 2005/0015005 A1 | 1/2005 | Kockro |
| 2005/0027492 A1 | 2/2005 | Taylor et al. |
| 2005/0059879 A1 | 3/2005 | Sutherland et al. |
| 2005/0070916 A1 | 3/2005 | Hollstien et al. |
| 2005/0075561 A1 | 4/2005 | Golden |
| 2005/0075562 A1 | 4/2005 | Szakelyhidi et al. |
| 2005/0128184 A1 | 6/2005 | Mcgreevy |
| 2005/0182315 A1 | 8/2005 | Ritter et al. |
| 2005/0245821 A1 | 11/2005 | Govari et al. |
| 2005/0273130 A1 | 12/2005 | Sell |
| 2006/0011999 A1 | 1/2006 | Schott et al. |
| 2006/0020213 A1 | 1/2006 | Whitman et al. |
| 2006/0030753 A1 | 2/2006 | Boutillette et al. |
| 2006/0084867 A1 | 4/2006 | Tremblay et al. |
| 2007/0161888 A1 | 7/2007 | Sherman et al. |
| 2007/0163367 A1 | 7/2007 | Sherman et al. |
| 2007/0167703 A1 | 7/2007 | Sherman et al. |
| 2007/0167741 A1 | 7/2007 | Sherman et al. |
| 2007/0270722 A1 | 11/2007 | Loeb et al. |
| 2008/0004516 A1 | 1/2008 | Disilvestro et al. |
| 2008/0012558 A1 | 1/2008 | Rossler et al. |
| 2008/0154127 A1 | 6/2008 | Disilvestro et al. |
| 2009/0189603 A1 | 7/2009 | Sherman et al. |
| 2022/0125517 A1* | 4/2022 | Zimmermann ........ A61B 34/30 |
| 2022/0142710 A1 | 5/2022 | Janna et al. |
| 2023/0165482 A1* | 6/2023 | Mahfouz .............. A61B 5/1114 703/2 |
| 2024/0153111 A1* | 5/2024 | Kaeseberg ................ G06T 7/30 |

FOREIGN PATENT DOCUMENTS

| | | |
|---|---|---|
| DE | 4014947 A1 | 11/1991 |
| DE | 10037491 A1 | 2/2002 |
| EP | 983018 A1 | 3/2000 |
| EP | 993804 A1 | 4/2000 |
| EP | 1020734 A2 | 7/2000 |
| EP | 1081647 A1 | 3/2001 |
| EP | 1181812 A1 | 2/2002 |
| EP | 1181891 A2 | 2/2002 |
| EP | 1184684 A2 | 3/2002 |
| EP | 1222636 A1 | 7/2002 |
| EP | 1302172 A1 | 4/2003 |
| EP | 1348394 A1 | 10/2003 |
| EP | 1447055 A1 | 8/2004 |
| EP | 1498851 A1 | 1/2005 |
| EP | 1530057 A2 | 5/2005 |
| EP | 1570781 A1 | 9/2005 |
| EP | 1580986 A2 | 9/2005 |
| EP | 1493384 B1 | 3/2009 |
| GB | 1283521 A | 7/1972 |
| GB | 2102127 A | 1/1983 |
| JP | 2004283606 A | 10/2004 |
| WO | 9304628 A1 | 3/1993 |
| WO | 9509562 A1 | 4/1995 |
| WO | 9608999 A1 | 3/1996 |
| WO | 9641119 A1 | 12/1996 |
| WO | 9748438 A2 | 12/1997 |
| WO | 9749445 A1 | 12/1997 |
| WO | 9832387 A1 | 7/1998 |
| WO | 9849938 A1 | 11/1998 |

(56) References Cited

FOREIGN PATENT DOCUMENTS

| | | |
|---|---|---|
| WO | 9852466 A1 | 11/1998 |
| WO | 9949783 A1 | 10/1999 |
| WO | 9959106 A1 | 11/1999 |
| WO | 0015286 A1 | 3/2000 |
| WO | 027281 A1 | 5/2000 |
| WO | 0051514 A1 | 9/2000 |
| WO | 0065981 A2 | 11/2000 |
| WO | 0074372 A1 | 12/2000 |
| WO | 0117600 A1 | 3/2001 |
| WO | 0122368 A1 | 3/2001 |
| WO | 0124697 A1 | 4/2001 |
| WO | 0130257 A1 | 5/2001 |
| WO | 0237935 A2 | 5/2002 |
| WO | 02062249 A1 | 8/2002 |
| WO | 02103618 A1 | 12/2002 |
| WO | 03051514 A1 | 6/2003 |
| WO | 03090022 A2 | 10/2003 |
| WO | 03096870 A2 | 11/2003 |
| WO | 2004095044 A1 | 11/2004 |
| WO | 2005013001 A2 | 2/2005 |
| WO | 2005044081 A2 | 5/2005 |
| WO | 2005067563 A2 | 7/2005 |
| WO | 2005084572 A2 | 9/2005 |
| WO | 2005086062 A2 | 9/2005 |
| WO | 2005087125 A2 | 9/2005 |
| WO | 2005119505 A2 | 12/2005 |
| WO | 2007011306 A2 | 1/2007 |
| WO | 2017204832 A1 | 11/2017 |

OTHER PUBLICATIONS

Prakash, N., Localization of a Magnetic Marker for GI Motility Studies: An In Vitro Feasibility Study, IEEE, 1007, pp. 2394-2397.
Raab, F., "Magnetic Position and Orientation Tracking System," 1979, IEEE, vol. 15, No. 5, pp. 709-717.
Schlageter, V., "Tracking system with five degrees of freedom using a 2D-array of Hall sensors and a permanent magnet," 2001, Elsevier, pp. 37-42.
Schlageter, V., Tracking system with five degrees of freedom using a 2D-array of Hall sensors and a permanent magnet, pp. 679-682, From the 14th European conference on Solid-State Transducers, Aug. 27-30, 2000, Copenhagen, Denmark, ISBN No. 87-89935-50-0.
Ybukami, S., "Motion Capture System of Magnetic Makers Using Three-Axial Magnetic Field Sensor," 2000, IEEE, vol. 36, No. 5, pp. 3646-3648.
Australian Office Action for Australian Patent Application No. 2006252293, May 18, 2010, 5 pgs.
Australian Office Action for Australian Patent Application No. 2006252294, Jun. 1, 2010, 2 pgs.
Australian Office Action for Australian Patent Application No. 2006252291, Apr. 13, 2011, 4 pgs.
European Search Report for European Patent Application No. 06256541.1-1265, Apr. 17, 2007, 9 pgs.
European Search Report for European Application No. 06256549.4-2318, May 10, 2007, 11 pgs.
European Search Report for European Application No. 06256574.2-1526, Feb. 12, 2008, 6 pgs.
European Search Report for European Patent Application No. 06256546.0-2310, Apr. 15, 2008, 7 pgs.
European Search Report for European Patent Application No. 06256546.0-2310/1803413, Jul. 16, 2008, 15 pgs.
European Search Report for European Patent Application No. 07255016.3-2218, Apr. 18, 2008, 6 pages.
Office Action for European Patent Application No. 06256549.4-2310, Jul. 13, 2009, 4 pgs.
Ip et al., "Arbitrary Facial Views Generation from Two Orthogonal Facial Images", IEEE, 1995, pp. 1079-1084.
Nikkhahe-Dehkordi et al., "3D Reconstruction of the Femoral Bone using Two X-ray Images from Orthogonal Views", Article retrieved from http://www.lab3d.odont.ku.dk/Documents/Pubs-96/FemurCAR96/femur.html , Elsevier Science V., 1996, 1 pg.
Lötjönen et al., "Reconstruction of 3-D Geometry Using 2-D Profiles and a Geometric Prior Model", IEEE Transactions on Medical Imaging, vol. 18, No. 10, Oct. 1999, 11 pages.
S. Delorme, "Three-Dimensional Modelling and Rendering of the Human Skeletal Trunk from 2D Radiographic Images", Abstract retrieved from http://doi.ieeecomputersociety.org/10/1109/IM.1999.805382 , 9 pgs.
Andrés del Valle et al., "3D Talking Head Customization by Adaptating a Generic Model to One Uncalibrated Picture", IEEE, 2001, pp. II-325-328.
Messmer et al., "Volumetric Model Determination of the Tibia Based on 2D Radiographs Using a 2D/3D Database", Computer Aided Surgery, vol. 6, 2001, pp. 183-194.
Benameur et al., "3D Biplanar Reconstruction of Scoliotic Vertebrae Using Statistical Models", Abstract retrieved from http://doi.ieeecomputersociety.org/10.1109/CVPR.2001.991014 , 7 pgs.
Laporte et al., "A biplanar reconstruction method based on 2D and 3D contours: application to the distal femur", Computer Methods in Biomechanics and Biomedical Engineering (Abstract Only), Feb. 2003, vol. 6, No. 1, 7 pgs.
Yao et al., "Assessing Accuracy Factors in Deformable 2D/3D Medical Image Registration Using a Statistical Pelvis Model", Abstract retrieved from http://doi.ieeecomputersociety.org/10.1109/ICCV.2003.1238644 , IEEE Computer Society, 6 pgs.
Livyatan et al., "Gradient-Based 2-D/3-D Rigid Registration of Fluoroscopic X-Ray to CT", IEEE Transactions on Medical Imaging; vol. 22, No. 11, Nov. 2003, pp. 1395-1406.
Rajamani, "A Novel Approach to Anatomical Structure Morphing for Intraoperative Visualization", Medical Image Computing and Computer-Assisted Intervention—MICCAI 2004, 2004 Proceedings, Part II, LNCS 3217, pp. 478-485.
Wu et al., "A Two-Level Method for Building a Statistical Shape Atlas", The Robotics Institute, Carnegie Mellon University, Pittsburgh, PA and CAOS: Institute for Computer Assisted Orthopaedic Surgery, The Western Pennsylvania Hospital, Pittsburgh, PA, 2005, Jun. 2005, 2 pgs.
Extended European Search Reoprt for European Patent Application No. 07252633.8-2310 / 1872737, Feb. 18, 2009, 11 pgs.
Besl et al., A Method for Registration of 3-D Shapes, 14 IEEE Trans. on Pattern Anal. & Machine Intelligence 239, Feb. 1992, 18 pages.
International Search Report for International Application No. PCT/EP2024/052877, Apr. 30, 2024, 5 pages.
Written Opinion of the International Searching Authority for International Application No. PCT/EP2024/052877, Apr. 30, 2024, 6 pages.

* cited by examiner

SYSTEMS AND METHODS FOR BONE MODEL REGISTRATION WITH ADAPTIVE SOFT TISSUE THICKNESS

TECHNICAL FIELD

The present disclosure relates generally to orthopaedic surgical tools and systems and, more particularly, to systems and methods for registering a bone model with patient anatomy for use during an orthopaedic surgical procedure.

BACKGROUND

Joint arthroplasty is a well-known surgical procedure by which a diseased and/or damaged natural joint is replaced by a prosthetic joint, which may include one or more orthopaedic implants. To facilitate the replacement of the natural joint with the prosthetic joint, orthopaedic surgeons may use a variety of orthopaedic surgical instruments such as, for example, surgical saws, cutting guides, reamers, broaches, drill guides, drills, positioners, insertion tools and/or other surgical instruments. A surgeon may use manual instruments such as cutting blocks or other cutting guides to perform the various resections in an orthopaedic procedure. Alternatively, or in addition, a surgeon may use a computer-assisted surgical navigation system, such as a robotic-assisted surgical system, to perform the various resections in an orthopaedic procedure.

SUMMARY

According to one aspect, a bone model registration method performed by a computing device may comprise defining a surgical coordinate system relative to a bone of a patient, capturing a plurality of point positions in the surgical coordinate system, identifying an estimated soft tissue thickness value for each of the plurality of point positions, and registering a three-dimensional model of the patient's bone in the surgical coordinate system based on the plurality of point positions and the estimated soft tissue thickness values. Each of the plurality of point positions may be associated with an anatomical landmark of the patient's bone. The plurality of point positions may comprise a first point position representing a location on a soft tissue surface covering a portion of the patient's bone.

In some embodiments, capturing the plurality of point positions may comprise tracking a location of a registration tool having a pointer using a camera array coupled to the computing device. The pointer of the registration tool may directly contact the soft tissue surface but not directly contact a surface of the patient's bone while the first point position is captured. In some embodiments, the plurality of point positions may further comprise a second point position captured while the pointer of the registration tool directly contacts the patient's bone. In some embodiments, identifying an estimated soft tissue thickness value for each of the plurality of point positions may comprises identifying the estimated soft tissue thickness value for the first point position as a number greater than zero and identifying the estimated soft tissue thickness value for the second point position as zero. In some embodiments, capturing the plurality of point positions may comprise moving the pointer of the registration tool along a surface of the patient's bone or along the soft tissue surface to capture a point cloud associated with an anatomical landmark.

In some embodiments, identifying an estimated soft tissue thickness value for each of the plurality of point positions may comprise receiving one or more estimates of soft tissue thickness from a surgeon during an orthopaedic surgical procedure. In some embodiments, identifying an estimated soft tissue thickness value for each of the plurality of point positions may comprise retrieving, from a memory device, one or more initial estimated soft tissue thickness values associated with the plurality of point positions.

In some embodiments, the method may further comprise receiving an updated estimated soft tissue thickness value for at least one of the plurality of point positions and re-registering the three-dimensional model of the patient's bone in the surgical coordinate system based on the plurality of point positions and the estimated soft tissue thickness values, including the at least one updated estimated soft tissue thickness value.

In some embodiments, registering the three-dimensional model may comprise determining, for each of the plurality of point positions, a distance between that point position and a corresponding point from the three-dimensional model extended by the estimated soft tissue thickness value associated with that point position, to determine a set of distances associated with a transformation of the three-dimensional model. Registering the three-dimensional model may further comprise optimizing the set the distances by iteratively adjusting the transformation of the three-dimensional model to improve registration quality of the three-dimensional model. Registering the three-dimensional model may further comprise optimizing the set the distances by iteratively adjusting the estimated soft tissue thickness values associated with one or more of the plurality of point positions to improve registration quality of the three-dimensional model.

In some embodiments, the method may further comprise displaying, after registering the three-dimensional model, a representation of the three-dimensional model in the surgical coordinate system. In some embodiments, the method may further comprise displaying the plurality of point positions relative to the displayed representation of the three-dimensional model. Displaying the plurality of point positions relative to the displayed representation of the three-dimensional model may comprise color-coding each of the plurality of point positions as a function of a distance between each point position and a corresponding point from the three-dimensional model extended by the estimated soft tissue thickness value associated with that point position.

In some embodiments, the method may further comprise, after registering the three-dimensional model, capturing a confirmation point position while a pointer of a registration tool contacts the soft tissue surface covering the portion of the patient's bone, displaying the confirmation point position relative to the displayed representation of the three-dimensional model, and displaying a difference between the confirmation point position and a corresponding point from the three-dimensional model extended by the estimated soft tissue thickness value associated with the corresponding point.

In some embodiments, displaying the difference between the confirmation point position and the corresponding point from the three-dimensional model extended by the estimated soft tissue thickness value associated with the corresponding point may comprise displaying the confirmation point position using a first color if the difference is less than a first threshold and displaying the confirmation point position using a second color if the difference is greater than the first threshold, where the second color is different from the first color.

In some embodiments, the method may further comprise, creating the three-dimensional model based on one or more preoperative medical images. In some embodiments, the method may further comprise, controlling a robotic surgical device in the surgical coordinate system based on the three-dimensional model after registering the three-dimensional model.

According to another aspect, an orthopaedic surgical system may comprise a computer system configured to define a surgical coordinate system relative to a bone of the patient, capture a plurality of point positions in the surgical coordinate system, identify an estimated soft tissue thickness value for each of the plurality of point positions, and register a three-dimensional model of the patient's bone in the surgical coordinate system based on the plurality of point positions and the estimated soft tissue thickness values. Each of the plurality of point positions may be associated with an anatomical landmark of the patient's bone. The plurality of point positions may comprise a first point position representing a location on a soft tissue surface covering a portion of the patient's bone.

In some embodiments, the system may further comprise a registration tool having a pointer configured to be contacted with various locations on a patient's anatomy. The system may further comprise a camera array coupled to the computing device. The computing device may be configured to capture the plurality of point positions by tracking a location of the registration tool using the camera array. The computing device may be configured to capture the first point position while the pointer of the registration tool directly contacts the soft tissue surface but does not directly contact the patient's bone.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
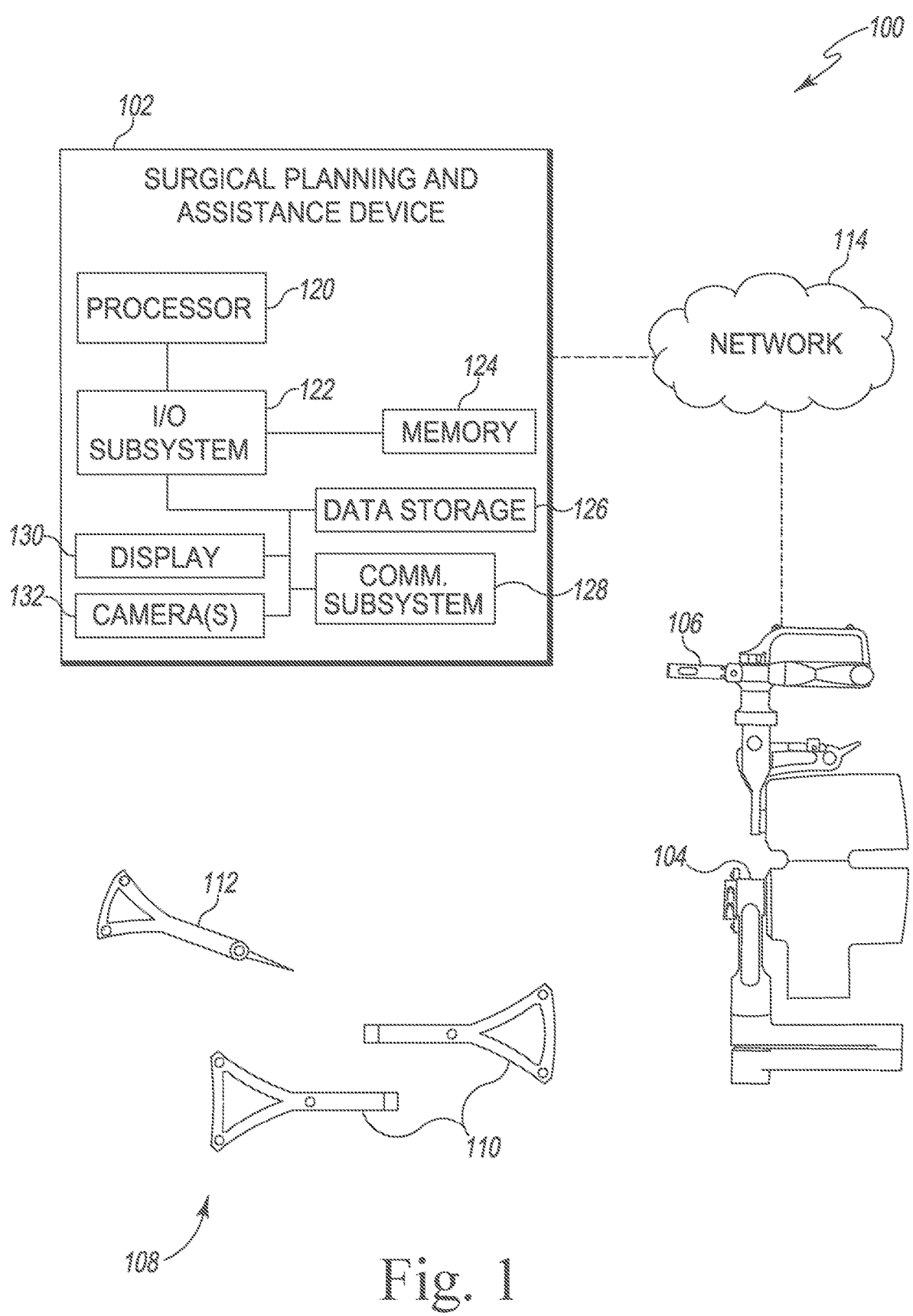
FIG. 1 is a schematic diagram of a system for planning and assisting an orthopaedic surgical procedure.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a surgical system 100 is used during an orthopaedic surgical procedure, such as a total knee arthroplasty (TKA) procedure, a total hip arthroplasty (THA) procedure, or a total shoulder arthroplasty (TSA) procedure. During that procedure, an orthopaedic surgeon performs registration of the patient's anatomy with the system 100. During registration, the system 100 determines thickness of cartilage or other soft tissue covering the patient's bone using a surgeon-driven process or an automated process as described further below. Registration aligns a three-dimensional model of the patient's bony anatomy with the patient's actual anatomy, for example by aligning the model in a surgical coordinate system. The surgeon or other user continues to create and/or modify a surgical plan based on the registration, and a robotic surgical device 104 may be controlled based on the surgical plan during operation of the surgical procedure, for example by robotically constraining a surgical saw 106 to one or more predetermined safe zones defined by the surgical plan.

Accordingly, the system 100 performs registration of a bone model while taking into account variable cartilage/soft tissue thickness, which is an improvement over prior processes. For example, compared to certain typical bone model registration processes, the system 100 does not require the surgeon to remove or pierce cartilage/soft tissue to contact bone while performing registration. Thus, the system 100 may reduce required surgical time and/or reduce surgical variability. As another example, the system 100 does not require use of a cartilage model derived from the bone model (e.g., based on a statistical shape model or other approach). As compared to typical approaches using a cartilage model, the system 100 may provide improved registration accuracy, and the system 100 may account for specificities such as local cartilage damage that are not included in a cartilage model.

As shown in FIG. 1, the system 100 includes the surgical planning and assistance device 102 and the robotic surgical device 104 as well as multiple registration tools 108. The surgical planning and assistance device 102 may be embodied as any type of computer system capable of performing the functions described herein. For example, the surgical planning and assistance device 102 may be embodied as, without limitation, a workstation, a desktop computer, a laptop computer, a special-purpose compute device, a server, a rack-mounted server, a blade server, a network appliance, a web appliance, a tablet computer, a smartphone, a consumer electronic device, a distributed computing system, a multiprocessor system, and/or any other computing device capable of performing the functions described herein. Additionally, although the surgical planning and assistance device 102 is illustrated in FIG. 1 as embodied as a single computer, it should be appreciated that the surgical planning and assistance device 102 may be embodied as multiple devices cooperating together to facilitate the functionality described below. For example, in some embodiments, the system 100 may include a base station and a satellite station or other combination of computing devices. Additionally or alternatively, in some embodiments, the surgical planning and assistance device 102 may be embodied as a "virtual server" formed from multiple computer systems distributed across a network and operating in a public or private cloud.

As shown in FIG. 1, the illustrative surgical planning and assistance device 102 includes a processor 120, an I/O subsystem 122, memory 124, a data storage device 126, and a communication subsystem 128. Of course, the surgical planning and assistance device 102 may include other or additional components, such as those commonly found in a computer (e.g., various input/output devices), in other embodiments. Additionally, in some embodiments, one or more of the illustrative components may be incorporated in, or otherwise form a portion of, another component. For example, the memory 124, or portions thereof, may be incorporated in the processor 120 in some embodiments.

The processor 120 may be embodied as any type of processor or controller capable of performing the functions described herein. For example, the processor may be embodied as a single or multi-core processor(s), digital signal processor, microcontroller, or other processor or processing/controlling circuit. Similarly, the memory 124 may be embodied as any type of volatile or non-volatile memory or data storage capable of performing the functions described herein. In operation, the memory 124 may store various data and software used during operation of the surgical planning and assistance device 102 such as operating systems, applications, programs, libraries, and drivers. The memory 124 is communicatively coupled to the processor 120 via the I/O subsystem 122, which may be embodied as circuitry and/or components to facilitate input/output operations with the processor 120, the memory 124, and other components of the surgical planning and assistance device 102. For example, the I/O subsystem 122 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 122 may form a portion of a system-on-a-chip (SoC) and be incorporated, along with the processor 120, the memory 124, and other components of the surgical planning and assistance device 102, on a single integrated circuit chip.

The data storage device 126 may be embodied as any type of device or devices configured for short-term or long-term storage of data such as, for example, memory devices and circuits, memory cards, hard disk drives, solid-state drives, or other data storage devices. The communication subsystem 128 of the surgical planning and assistance device 102 may be embodied as any communication circuit, device, or collection thereof, capable of enabling communications between the surgical planning and assistance device 102 and remote devices. The communication subsystem 128 may be configured to use any one or more communication technology (e.g., wireless or wired communications) and associated protocols (e.g., Ethernet, Bluetooth®, Wi-Fi®, WiMAX, etc.) to effect such communication.

As shown in FIG. 1, the surgical planning and assistance device 102 includes a display 130. The display 130 may be embodied as any type of display capable of displaying digital images or other information, such as a liquid crystal display (LCD), a light emitting diode (LED), a plasma display, a cathode ray tube (CRT), or other type of display device. In some embodiments, the display 130 may be coupled to a touch screen to allow user interaction with the surgical planning and assistance device 102.

The surgical planning and assistance device 102 further includes one or more cameras 132. Each of the cameras 132 may be embodied as a digital camera or other digital imaging device coupled to the surgical planning and assistance device 102. Each camera 132 includes an electronic image sensor, such as an active-pixel sensor (APS), e.g., a complementary metal-oxide-semiconductor (CMOS) sensor, or a charge-coupled device (CCD). In the illustrative embodiment, multiple cameras 132 are arranged in an array and are thus capable of determining distance to objects imaged by the cameras 132.

The robotic surgical device 104 may be embodied as any type of robot capable of performing the functions described herein. Illustratively, the robotic surgical device 104 is embodied as a robotic arm that may be attached to a surgical table or otherwise positioned near a patient during an orthopaedic surgical procedure. The robotic surgical device 104 includes a surgical tool 106, illustratively embodied as a surgical saw 106. In use, the robotic surgical device 104 supports the surgical saw 106 and may constrain movement of the surgical saw 106 within a resection plane specified in a surgical plan, as described further below. The surgeon may activate the surgical saw 106 and perform the resection with the surgical saw 106 while the robotic surgical device 104 constrains movement of the surgical saw 106 to the resection plane. Although illustrated with a surgical saw 106, it should be understood that, in other embodiments, the robotic surgical device 104 may include, or be used with, one or more other surgical instruments, such as, for example, surgical burrs, chisels, impactors, reamers, and other powered surgical tools. The robotic surgical device 104 may illustratively be embodied as a VELYS™ Robotic-Assisted Solution, commercially available from DePuy Synthes Products, Inc. of Warsaw, Indiana.

The surgical planning and assistance device 102 and the robotic surgical device 104 may be configured to transmit and receive data with each other and/or other devices of the system 100 over a network 114. The network 114 may be embodied as any number of various wired and/or wireless networks. For example, the network 114 may be embodied as, or otherwise include, a wired or wireless local area network (LAN), a wired or wireless wide area network (WAN), a cellular network, and/or a publicly-accessible, global network such as the Internet. As such, the network 114 include any number of additional devices, such as additional computers, routers, stations, and switches, to facilitate communications among the devices of the system 100.

As shown in FIG. 1, the system 100 further includes a number of registration tools 108. As described further below, in use, the surgical planning and assistance device 102 may track the location of the registration tools 108 in space using the array of cameras 132. For example, each registration tool 108 may include a number of hydrophobic optical reflectors arranged in a predetermined pattern visible to the cameras 132. Illustratively, the registration tools 108 include a plurality of arrays 110 configured to each be secured to one of the patient's bones, to the robotic surgical device 104, or to the surgical tool 106. Illustratively, the registration tools 108 also include a pointer 112 configured to be temporarily positioned by a surgeon relative to anatomical landmarks of the patient (e.g., with an end of the pointer 112 in contact those anatomical landmarks) while the pointer 112 is observed by the cameras 132. As such, the registration tools 108 may be used for registration and tracking of the patient's bony anatomy during the orthopaedic surgical procedure. Although illustrated as including registration tools 108 suitable for optical tracking with the cameras 132, it should be understood that in some embodiments, the system 100 may use electromagnetic tracking or other position tracking technology for tracking the registration tools 108.

Figure 2:
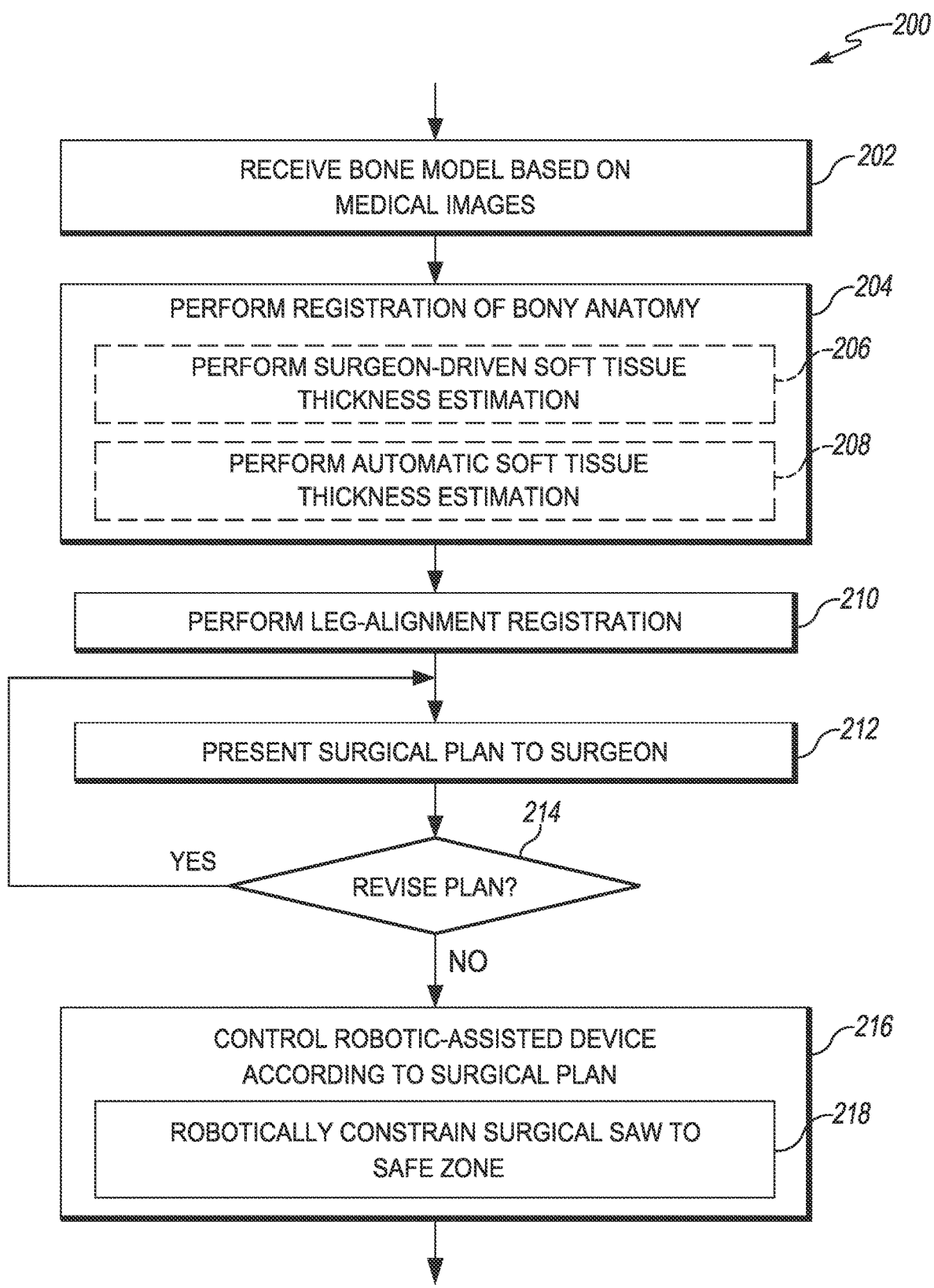
FIG. 2 is a simplified flow diagram of a method for an orthopaedic surgical procedure including bone model registration that may be executed by a surgical planning and assistance device of FIG. 1.

Referring now to FIG. 2, in use, the surgical planning and assistance device 102 may perform a method 200 for an orthopaedic surgical procedure with automated bone model registration. The method 200 begins with block 202, in which the device 102 receives a bone model that is generated based on one or more medical images. The bone model may be embodied as a three-dimensional computer model of the patient's bony anatomy, including one or more bone surfaces. For example, in some embodiments, the bone model may include a triangular mesh representative of the bone surface. The bone model may be generated preoperatively based on one or more medical images. The medical images may include images generated using computerized tomography (CT) scan imagery, orthogonal X-ray imagery, magnetic resonance imaging (MRI), ultrasound, or other imaging techniques. As an illustrative example, a computing device or other modeling system (e.g., surgical planning and assistance device 102 or another device) may perform an x-ray segmentation process to model the patient's bone based on input medical images. In that segmentation process, the device receives a set of x-ray images. The device accesses a bone library that includes models or other measurements of many sample bones. The device generates a three-dimensional model based on the bone library and then morphs (interpolates) that model to match the patient's specific geometry represented in the medical images.

In block 204, the device 102 performs registration of the patient's bony anatomy. In the illustrative embodiment, block 204 involves the surgeon attaching a bone array 110 to each of the patient's tibia and femur. The surgeon may use the pointer 112 to touch various landmarks on the patient's bony anatomy. During this process, the device 102 uses the cameras 132 to track the positions of the bone arrays 110 and the pointer 112 and thus registers the position of each landmark of the patient's bony anatomy. Thus, the device 102 may capture multiple point positions in a surgical coordinate system relative to the patient's bone (e.g., relative to bone arrays 110 fixed to the patient's bone). It is contemplated that, in other embodiments, the device 102 may perform registration of the patient's bony anatomy using a non-contact registration tool, such as a laser or white-light scanner or an ultrasound device that identifies surfaces of the patient's anatomy using light or sound waves. Although the remainder of the present disclosure generally refers to the use of a registration tool or pointer 112 configured to be contacted with various locations on a patient's anatomy, embodiments according to the present disclosure may also be used with non-contact registration tools. As described further below, the device 102 may register the three-dimensional bone model to the same surgical coordinate system as the patient's bone by matching features of the bone model to corresponding landmarks on the patient's bone.

Figure 3A:
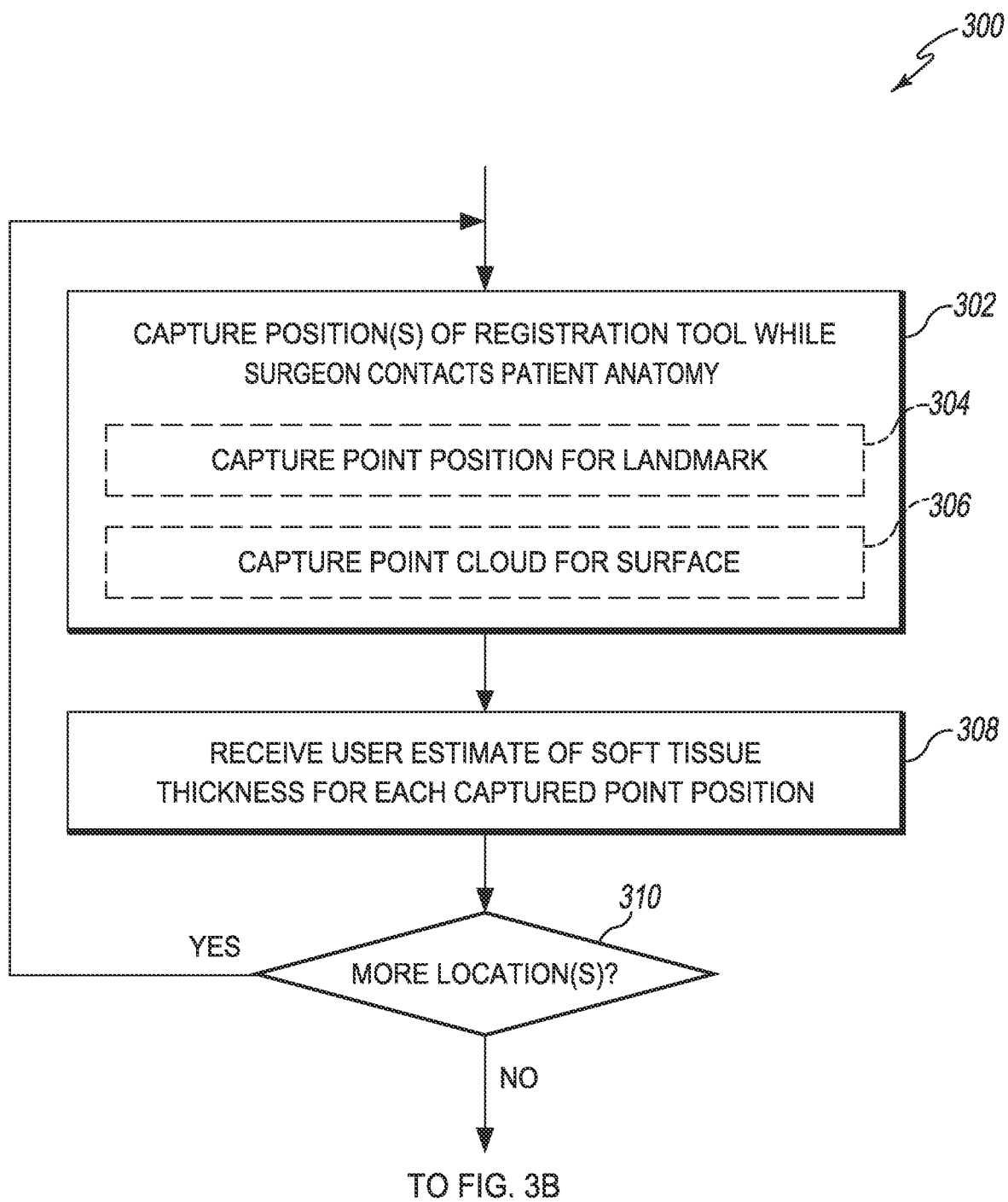
FIGS. 3A, 3B, and 3C are a simplified flow diagram of a method for bone model registration with surgeon-driven cartilage thickness estimation that may be executed by the surgical planning and assistance device of FIG. 1.
Figure 3B:
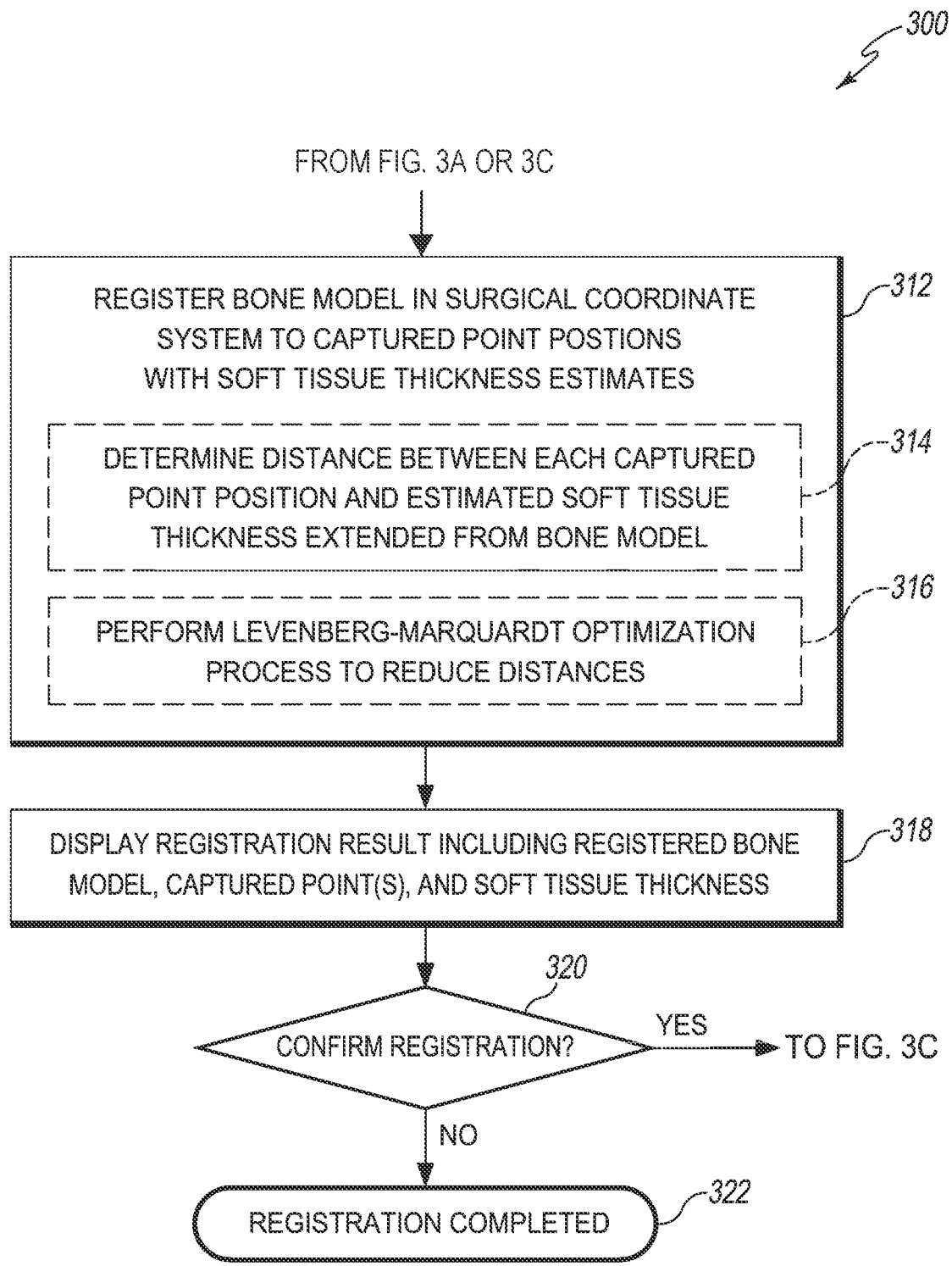
Figure 3C:
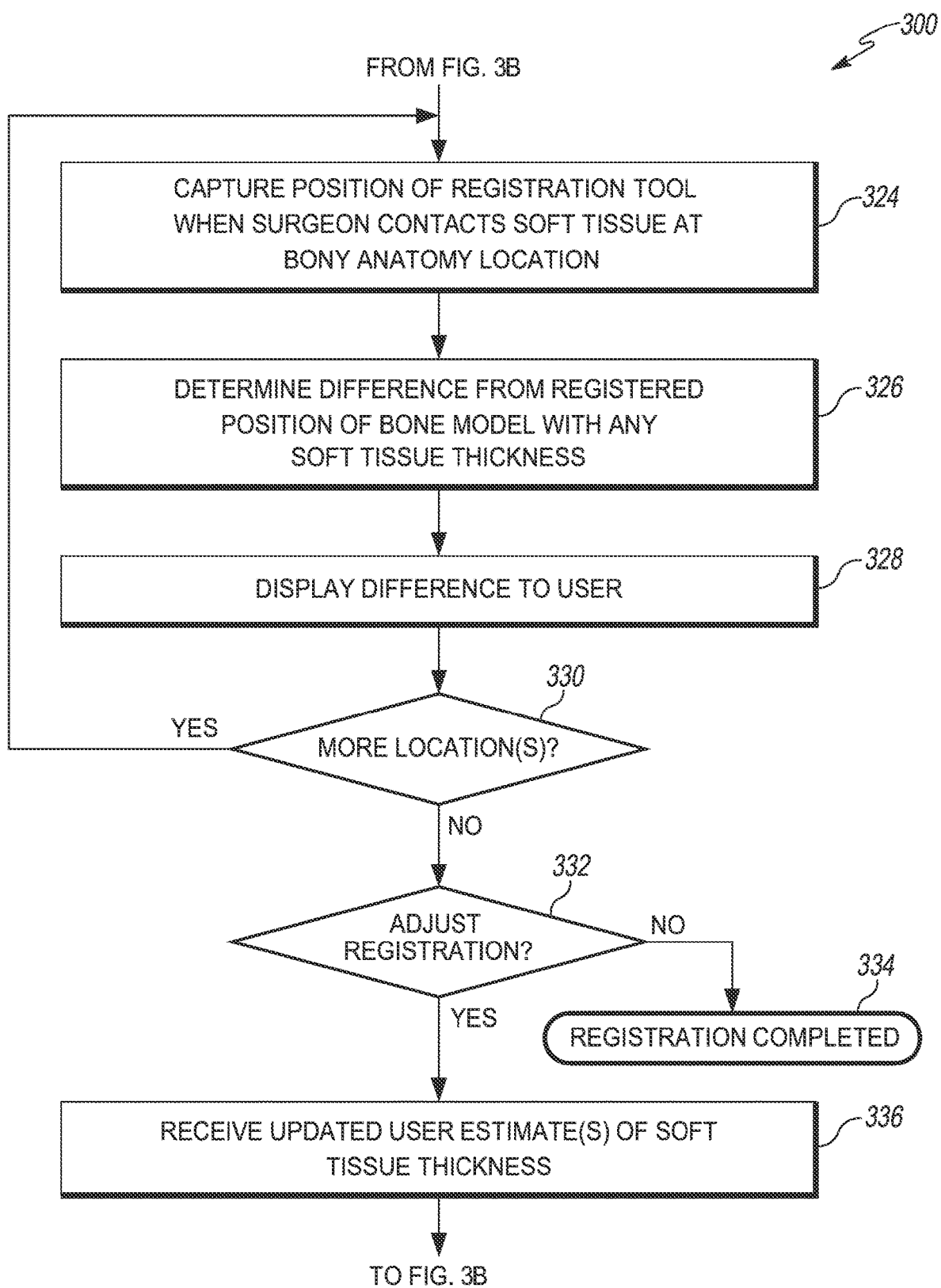
Figure 4A:
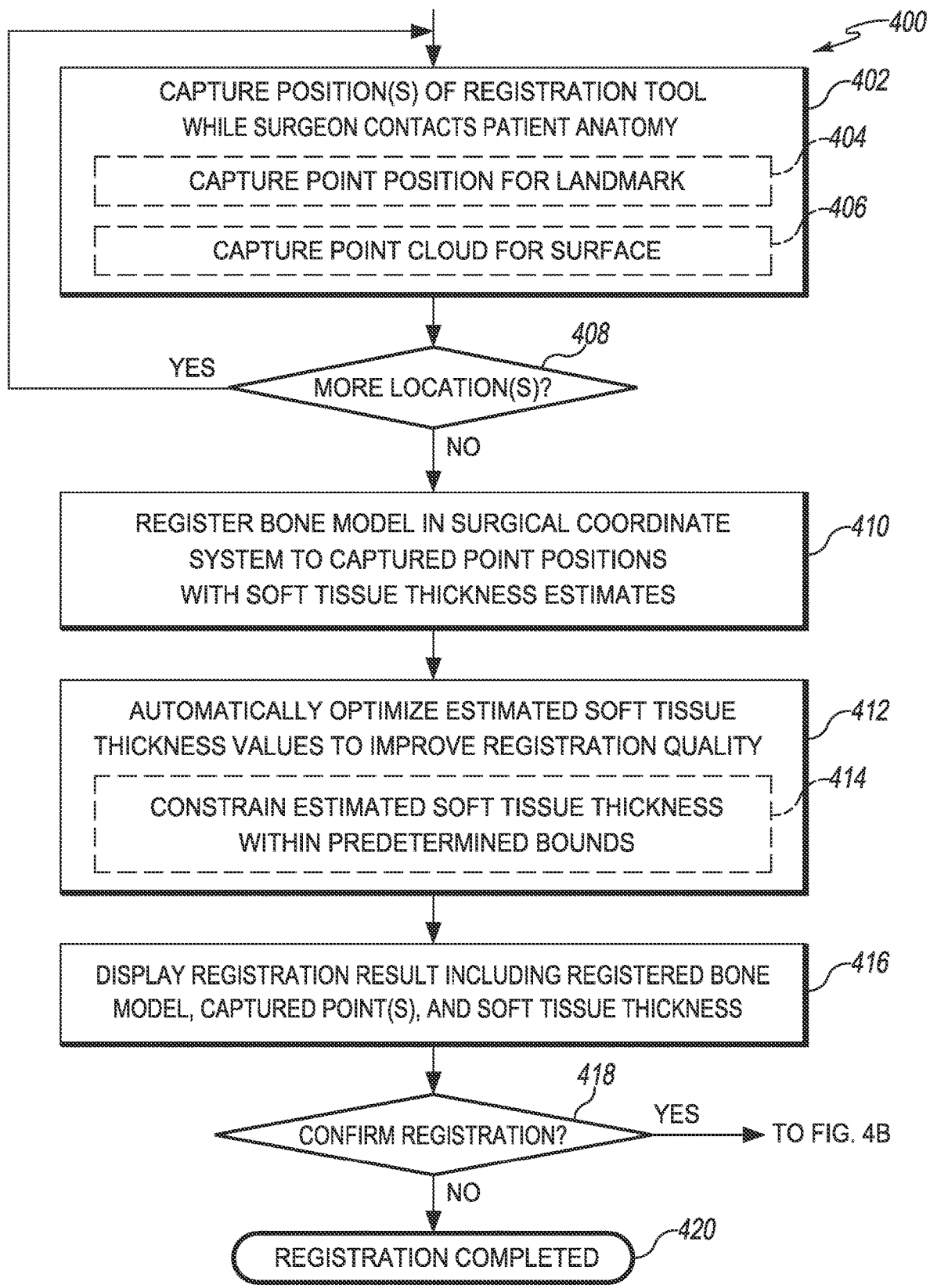
FIGS. 4A and 4B are a simplified flow diagram of a method for bone model registration with automated cartilage thickness estimation that may be executed by the surgical planning and assistance device of FIG. 1.
Figure 4B:
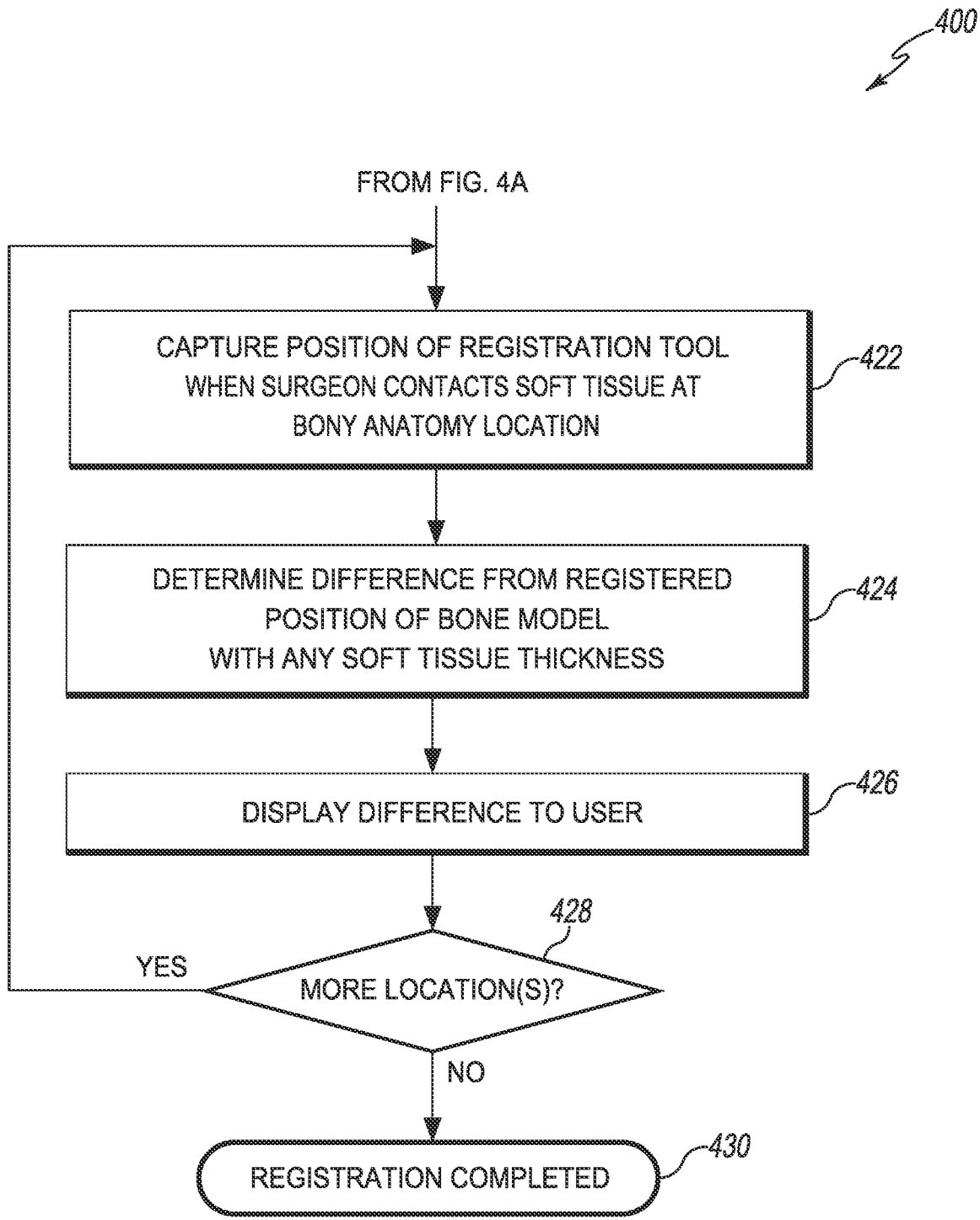

As part of bony registration, the device 102 may perform an automated soft tissue thickness estimation process. During this process, the thickness of cartilage or other soft tissue covering portions of the patient's bone may be taken into account during the registration process. The surgeon may verify the estimated soft tissue thickness, for example by using the pointer 112 to touch soft tissue covering various portions of the patient's bony anatomy and verifying the reported position 112 relative to the bone model. In some embodiments, the device 102 may perform a surgeon-driven soft tissue thickness estimation process in block 206. One potential embodiment of a surgeon-driven process is shown in FIGS. 3A-3C and described below. Additionally or alternatively, in some embodiments, the device 102 may perform an automatic soft tissue thickness estimation process in block 208. One potential embodiment of an automatic process is shown in FIGS. 4A-4B and described below.

During bony registration or at another time, the device 102 may prompt the surgeon or other user to verify an implant size to be used in the orthopaedic surgical procedure. The implant size may be predetermined during preoperative planning or otherwise set to an initial value. After prompting, the surgeon or other user may select a different implant size, which is stored by the device 102 for further processing.

In block 210, in some embodiments, the device 102 may perform leg-alignment registration to assess the balance of the patient's knee joint throughout a range of motion (e.g., for a TKA surgical procedure). To perform the leg-alignment registration, the surgeon may articulate the patient's knee joint through the range of motion while the device 102 uses the cameras 132 to track the position of the bone arrays 110 and thus registers the relative positions of the femur and the tibia at multiple points in the range of motion. In In some surgeries, the surgeon may perform soft-tissue release, in which case the leg-alignment registration may be repeated.

In block 212, the device 102 presents a surgical plan for review by the surgeon. The surgical plan may include information indicating the type, size, and position of one or more implants. For example, in a TKA surgical procedure, the surgical plan may include one or more tibial or femoral resection heights, femoral component rotation, femoral component flexion, femoral component anterior/posterior shift, tibial slope, and/or varus/*valgus* angle. The surgical plan may include similar information tailored for other surgical procedures. The surgical plan may be generated preoperatively or, in some embodiments, may be generated and/or modified automatically and/or interactively by the surgeon using the device 102.

The device 102 may use any input/output device or output modality to present the surgical plan. In some embodiments, the device 102 may display numerical dimensions for resection heights, angles, position shifts, or other parameters of the surgical plan using the display 130. In some embodiments, the device 102 may graphically display the dimensions of the surgical plan using the display 130. For example, the device 102 may graphically render three-dimensional models of the patient's bony anatomy along with virtual prosthetic components that are positioned relative to the bony anatomy according to the surgical plan. In some embodiments, the device 102 may graphically display the surgical plan (including models of the patient's bony anatomy and/or the virtual prosthetic components) using an augmented reality device and/or a virtual reality device (e.g., a head-mounted stereo display).

In block 214, the device 102 receives input regarding whether the surgeon wishes to revise the surgical plan. For example, the surgeon may revise the surgical plan by modifying one or more planned values of the surgical plan. As another example, the surgeon may adjust a particular planned resection height or angle. Alternatively, the surgeon may accept the surgical plan or otherwise indicate that no revisions are required. If the device 102 is instructed to revise the surgical plan, the method 202 loops back to block 212, in which the device 102 presents a revised surgical plan. If the device 102 determines not to revise the surgical plan, the method 200 advances to block 216.

In block 216, the device 102 controls the robotic surgical device 104 according to the surgical plan to assist the surgeon in performing the orthopaedic surgical procedure. The device 102 may transmit the surgical plan to the robotic surgical device 104 or otherwise cause the robotic surgical device 104 to operate according to the surgical plan. Illustratively, in block 218, the robotic surgical device 104 robotically constrains the surgical saw 106 to a predetermined safe zone, such as a predetermined resection plane. The safe zone may be identified in or otherwise determined based on the bone model that was registered with the patient's bony anatomy as described above. For example, the robotic surgical device 104 may constrain the surgical saw 106 to a predetermined safe zone defined by or relative to the bone model. The robotic surgical device 104 may locate this safe zone relative to the patient's anatomy by tracking the bone array 110 using the cameras 132 of the device 102 in the surgical coordinate system, similar to the bony registration process described above. After controlling the robotic surgical device 104, the method 200 is completed. The surgeon may continue the orthopaedic surgical procedure, for example by installing one or more trial components, one or more prosthetics, or otherwise completing the orthopaedic surgical procedure.

Referring now to FIGS. 3A-3C, in use, the surgical planning and assistance device 102 may perform a method 300 for bone model registration with surgeon-driven soft tissue thickness estimation. The method 300 may be executed in connection with bony registration as described above in connection with block 204 of FIG. 2. The method 300 begins with block 302, in which the device 102 captures one or more positions of a registration tool 108 (e.g., the pointer 112) when the surgeon contacts the registration tool 108 at a specified location on the patient's bony anatomy. The device 102 may display the specified location or otherwise prompt the surgeon with the specified location. For example, the surgeon may contact the pointer 112 directly on a surface of the patient's bone, or on cartilage, menisci, or other soft tissue covering the patient's bone, at a particular bony landmark. Advantageously, the method 300 does not require the surgeon to pierce cartilage, menisci, or other soft tissue covering the patient's bone, where present, to reach the underlying bone surface with the pointer 112. Instead, for such landmarks, the surgeon may contact the pointer 112 to the soft tissue surface (without directly contacting the bone surface), and the device 102 will account for the thickness of the soft tissue as described below.

As an illustrative example, for a TKA surgical procedure, the specified bony landmarks may include the tibial knee center, the tibial medial plateau, the tibial lateral plateau, the femoral knee center, Whiteside's line, the femoral medial epicondyle, the femoral lateral epicondyle, the femoral medial distal condyle, the femoral lateral distal condyle, the femoral medial posterior condyle, the femoral lateral posterior condyle, the femoral anterior cortex, and/or other identified locations of the patient's knee joint. As another illustrative example, for a TSA surgical procedure, the specified bony landmarks may include the humeral head, the humerus bicipital groove, the glenoid fossa, the acromion, and/or other identified locations of the patient's shoulder joint. As another illustrative example, for a THA surgical procedure, the specified bony landmarks may include the femoral head, the acetabulum, and/or other identified locations of the patient's hip joint.

Each of the captured positions of the registration tool 108 may be represented by coordinates in a surgical coordinate system relative to the patient's bone. For example, each captured position may be represented by a three-dimensional position relative to one or more of the arrays 110 fixed to the patient's bone. In some embodiments, the device 102 may capture a single point position for a particular landmark in block 304. For example, the device 102 may capture a particular point representing the location of the pointer 112 when positioned at the tibial knee center, the femoral knee center, or other predetermined location on the patient's bone (or soft tissue covering the patient's bone). In some embodiments, the device 102 may capture a point cloud for a surface that includes or is otherwise associated with a landmark in block 306. The point cloud may include many individual points captured as the surgeon moves the pointer 112 across the landmark and/or across soft tissue covering the landmark (or portions thereof). For example, the device 102 may capture a point cloud representing captured positions of the pointer 112 when moved across cartilage or other soft tissue covering the humeral head, one or more tibial plateaus, one or more femoral condyles, and/or other bone surfaces.

In block 308, the device 102 receives a user estimate of soft tissue thickness for each bony anatomy location for which the registration position(s) were captured as described above in connection with block 302. The estimated soft tissue thickness may be provided by the surgeon or other user using a touchscreen display 130 and/or other user interface provided by the device 102. For example, the surgeon may provide the estimated soft tissue thickness in millimeters for the cartilage or other soft tissue (if any) covering the landmark (e.g., the humeral head, the tibial plateau, the femoral condyle, or other landmark). For landmarks that are not covered by soft tissue (or very little soft tissue), the user estimate of soft tissue thickness may be zero. Additionally or alternatively, in some embodiments, the estimated soft tissue thickness may be determined from one or more surgeon preferences, which may include a set of parameters defined by the surgeon before starting the surgical procedure. In some embodiments, the estimated soft tissue thickness may be determined from a set of predetermined default values.

In block 310, the device 102 determines whether additional locations remain for registration. As described above, the device 102 may capture registration positions for one or more predetermined landmarks associated with the particular surgical procedure. If additional locations remain, the method 300 loops back to block 302. If no additional locations remain for registration, the method 300 advances to block 312.

In block 312, the device 102 registers the bone model in the surgical coordinate system to the captured point positions using the estimates of soft tissue thickness. The device 102 may register the bone model by determining a rigid transformation of the bone model that minimizes a distance, error, or other cost function between the bone model and the captured point positions, taking into account the estimated soft tissue thickness associated with each captured point position. In block 314, the device 102 may determine a distance between each captured point position and its estimated soft tissue thickness extended outward from the bone model. As described above, each landmark or other location in the patient's bony anatomy may be associated with a different estimated soft tissue thickness (including zero). Accordingly, the distance between point positions nearest to or otherwise associated with each landmark or other location may be determined with the corresponding estimated soft tissue thickness. In some embodiments of block 314, the device 102 may register the bone model in the surgical coordinate system using both captured point positions having soft tissue thickness estimates greater than zero and captured point positions having soft tissue thickness estimates of zero.

In block 316, the device 102 may perform a Levenberg-Marquardt optimization process (or other optimization process, such as an Iterative Closest Point algorithm) to register the bone model to the captured point positions. As part of this process, the device 102 may apply a rigid transformation to the bone model, determine a distance measure between each captured point position and a corresponding point of the bone model extended by the associated estimated soft tissue thickness, and then iteratively adjust the transformation to minimize that distance measure. The device 102 may continue optimizing registration of the bone model until a local or global minimum is found or the process otherwise converges.

In block 318, the device 102 displays registration results including the registered bone model, one or more captured point positions, and the estimated soft tissue thickness(es). Those registration results may be displayed as numerical results and/or graphical results. For example, in some embodiments, the device 102 may display a graphical representation of the bone model after being registered to the surgical coordinate system. The device 102 may display the soft tissue thickness as a three dimensional overlay on the bone model or otherwise graphically display the soft tissue thickness, and the device 102 may display the registration positions as individual points, point clouds, or other representations of the positions.

In block 320, the device 102 determines whether the surgeon requests to interactively confirm the registration. If not, the method 300 advances to block 322, in which the method 300 is completed. The surgical procedure may continue as described above in connection with FIG. 2. Referring again to block 320, if the surgeon requests to confirm the registration, the method 300 advances to block 324, shown in FIG. 3C.

In block 324, the device 102 captures a position of the registration tool 108 (e.g., the pointer 112) when the surgeon contacts the registration tool 108 on the patient's bone or on soft tissue covering a portion of the patient's bone. This capture process may be similar to the capture process performed during registration as described above in connection with block 302. In some embodiments, the device 102 may capture and process the position of the registration tool 108 in real time as the surgeon manipulates the tool 108. For example, the surgeon may contact the pointer 112 on cartilage, menisci, or other soft tissue covering the patient's bone at a particular bony landmark. That bony landmark may have been one of the bony landmarks specified for registration as described above in connection with block 302. Additionally, as described above, the captured position may be represented by coordinates in the surgical coordinate system relative to the patient's bone.

In some embodiments, block 324 (like block 302) may involve the device 102 capturing a position at a location on the patient's bony anatomy that is known to have no soft tissue or a small amount of soft tissue. For example, the device 102 may capture a position on the acromion on the patient's scapula. Such captured positions of locations with no soft tissue or a small amount of soft tissue may be useful for confirming proper registration of the bone model.

In block 326, the device 102 determines the difference between the point position captured in block 324 and a corresponding registered position of the bone model, incorporating the associated estimate of soft tissue thickness from block 308. For example, the device 102 may determine a distance, in the surgical coordinate system, between the point position captured in block 324 and a corresponding point that is either on the surface of the bone model (where the estimated soft tissue thickness for that point was zero) or extended from the surface of the bone model by the estimated soft tissue thickness (where the estimate was non-zero). That distance may be a shortest distance, an orthogonal distance, a distance in a predetermined direction, a height, or other measure of distance between the captured point position and the point in the surgical coordinate system represented by the bone model extended by the estimated soft tissue thickness. In that example, a smaller difference indicates that the position of the pointer 112 has a better match to the registered position of the bone model, accounting for any soft tissue, for that location. In other words, if the estimated soft tissue thickness matches the actual soft tissue thickness at that location, then the difference between the point position captured in block 324 and a corresponding point on the surface of the registered bone model plus the estimated soft tissue thickness will be zero or close to zero, indicating a good match between the registered bone model and the patient's actual bone.

In block 328, the device 102 displays the difference determined in block 326 to the surgeon and/or another user. Similar to the display of registration results described above in connection with block 318, the device 102 may display this difference numerically, graphically, or using any other technique. For example, the device 102 may display a distance determined in block 326 as a length in millimeters. As another example, the device 102 may graphically display the bone model along with one or more points, point clouds, surfaces, or other representations of the captured positions. In some embodiments, each point may be color-coded or otherwise marked to indicate a difference between the captured positions and the corresponding registered position of the bone model. For example, a point may be displayed in green when that difference is less than a first threshold (e.g., 0.7 mm, 1 mm, 2 mm, or a different threshold), yellow when that difference is greater than or equal to the first threshold and less than a second threshold (e.g., 1.4 mm, 2 mm, 3 mm, or a different threshold), and red when that difference is greater than or equal to the second threshold. The particular thresholds used for color-coding may be adjusted based on the estimated soft tissue thickness. As such, the device 102 may provide a "green" indication to indicate that the bone model registration is appropriate even when the pointer 112 touches soft tissue at a relatively large distance from the registered bone model surface (e.g., several millimeters).

In block 330, the device 102 determines whether additional locations remain for confirming the registration. The device 102 may verify registration for multiple predetermined landmarks associated with the particular surgical procedure, as described above. If additional locations remain, the method 300 loops back to block 324. If no additional locations remain for confirming the registration, the method 300 advances to block 332.

In block 332, the device 102 determines whether the surgeon requests to adjust the registration. If not, the method 300 advances to block 334, in which the method 300 is completed. The surgical procedure may continue as described above in connection with FIG. 2. Referring again to block 332, if the surgeon requests to adjust the registration, the method 300 advances to block 336.

In block 336, the device 102 receives an updated user estimate of soft tissue thickness for one or more bony anatomy locations. Illustratively, the updated user estimate is determined by the surgeon based on the interactive registration verification process described above. Each estimated soft tissue thickness may be provided by the surgeon or other user using the touchscreen display 130 and/or other user interface provided by the device 102. For example, the surgeon may provide the estimated soft tissue thickness in millimeters for the cartilage or other soft tissue covering a landmark (e.g., the humeral head, tibial plateau, femoral condyle, or other landmark). After receiving the updated estimated soft tissue thickness, the method 300 loops back to block 312, shown in FIG. 3B, in which the device 102 continues to register the bone model based on the updated point positions. Additionally or alternatively, although illustrated in FIGS. 3A-3C as updating the estimated soft tissue thickness after confirming registration for all of the bony landmarks, it should be understood that in some embodiments, the device 102 may receive an updated estimated soft tissue thickness after confirming less than all of the bony landmarks and continue to update the registration of the bone model as described above.

Referring now to FIGS. 4A and 4B, in use, the surgical planning and assistance device 102 may perform a method 400 for bone model registration with automatic soft tissue thickness estimation. The method 400 may be executed in connection with bony registration as described above in connection with block 204 of FIG. 2. The method 400 begins with block 402, in which the device 102 captures one or more positions of a registration tool 108 (e.g., the pointer 112) when the surgeon contacts the registration tool 108 at a specified location on the patient's bony anatomy. The device 102 may display the specified location or otherwise prompt the surgeon with the specified location. For example, the surgeon may contact the pointer 112 directly on a surface of the patient's bone, or on cartilage, menisci, or other soft tissue covering the patient's bone, at a particular bony landmark. Advantageously, the method 400 does not require the surgeon to pierce cartilage, menisci, or other soft tissue covering the patient's bone, where present, to reach the underlying bone surface with the pointer 112. Instead, for such landmarks, the surgeon may contact the pointer 112 to the soft tissue surface (without directly contacting the bone surface), and the device 102 will account for the thickness of the soft tissue as described below.

As an illustrative example, for a TKA surgical procedure, the specified bony landmarks may include the tibial knee center, the tibial medial plateau, the tibial lateral plateau, the femoral knee center, Whiteside's line, the femoral medial epicondyle, the femoral lateral epicondyle, the femoral medial distal condyle, the femoral lateral distal condyle, the femoral medial posterior condyle, the femoral lateral posterior condyle, the femoral anterior cortex, and/or other identified locations of the patient's knee joint. As another illustrative example, for a TSA surgical procedure, the specified bony landmarks may include the humeral head, the humerus bicipital groove, the glenoid fossa, the acromion, and/or other identified locations of the patient's shoulder joint. As another illustrative example, for a THA surgical procedure, the specified bony landmarks may include the femoral head, the acetabulum, and/or other identified locations of the patient's hip joint.

Each of the captured positions of the registration tool 108 may be represented by coordinates in a surgical coordinate system relative to the patient's bone. For example, each captured position may be represented by a three-dimensional position relative to one or more of the arrays 110 fixed to the patient's bone. In some embodiments, the device 102 may capture a single point position for a particular landmark in block 404. For example, the device 102 may capture a particular point representing the location of the pointer 112 when positioned at the tibial knee center, the femoral knee center, or other predetermined location on the patient's bone (or soft tissue covering the patient's bone). In some embodiments, the device 102 may capture a point cloud for a surface that includes or is otherwise associated with a landmark in block 406. The point cloud may include many individual points captured as the surgeon moves the pointer 112 across the landmark and/or across soft tissue covering the landmark (or portions thereof). For example, the device 102 may capture a point cloud representing captured positions of the pointer 112 when moved across cartilage or other soft tissue covering the humeral head, one or more tibial plateaus, one or more femoral condyles, and/or other bone surfaces.

In block 408, the device 102 determines whether additional locations remain for registration. As described above, the device 102 may capture registration positions for one or more predetermined landmarks associated with the particular surgical procedure. If additional locations remain, the method 400 loops back to block 402. If no additional locations remain for registration, the method 400 advances to block 410.

In block 410, the device 102 registers the bone model in the surgical coordinate system to the captured point positions using automatic estimates of soft tissue thickness. The device 102 may automatically associate an initial estimated soft tissue thickness (including zero) with each captured point position based on a standard anatomical model (which may be tuned to patient characteristics such as age, gender, height, weight, etc.). As described above, the device 102 may register the bone model by determining a rigid transformation of the bone model that minimizes a distance, error, or other cost functions between the bone model and the captured point positions, taking into account the estimated soft tissue thickness associated with each captured point. Accordingly, the distance between point positions nearest to or otherwise associated with each landmark or other location may be determined with the corresponding estimated soft tissue thickness. For example, in some embodiments, the device 102 may perform a Levenberg-Marquardt optimization process (or other optimization process, such as an Iterative Closest Point algorithm) to register the bone model to the captured point positions. In some embodiments of block 410, the device 102 may register the bone model in the surgical coordinate system using both captured point positions having soft tissue thickness estimates greater than zero and captured point positions having soft tissue thickness estimates of zero.

In block 412, the device 102 automatically optimizes the estimated soft tissue thickness values to improve registration quality. As part of the registration process, the device 102 may apply a rigid transformation to the bone model and determine a distance measure between each captured point position and a corresponding point of the bone model extended by the associated estimated soft tissue thickness. The device 102 may iteratively adjust the transformation and/or the estimated soft tissue thickness values at various locations to minimize the distance measure. The device 102 may use any appropriate optimization algorithm or other technique to adjust the estimated soft tissue thickness. In some embodiments, the device 102 may constrain the estimated soft tissue thickness within one or more predetermined bounds in block 414. The predetermined bounds represent realistic or otherwise likely values for soft tissue thickness, and each of those bounds may be associated with a particular bony landmark or other location. For example, in an embodiment the estimated cartilage thickness for the glenoid fossa may be constrained to values between 0 mm and 2 mm. The estimated cartilage thickness for each anatomical location may be set to an initial value typical for that anatomical location, and then may be optimized within the predetermined bounds.

In block 416, the device 102 displays registration results including the registered bone model, one or more captured point positions, and the estimated soft tissue thickness(es). Those registration results may be displayed as numerical results and/or graphical results. For example, in some embodiments, the device 102 may display a graphical representation of the bone model after being registered to the surgical coordinate system. The device 102 may display the soft tissue thickness as a three dimensional overlay on the bone model or otherwise graphically display the soft tissue thickness, and the device 102 may display the point positions as individual points, point clouds, or other representations of the positions.

In block 418, the device 102 determines whether the surgeon requests to interactively confirm the registration. If not, the method 400 advances to block 420, in which the method 400 is completed. The surgical procedure may continue as described above in connection with FIG. 2. Referring again to block 418, if the surgeon requests to confirm the registration, the method 400 advances to block 422, shown in FIG. 4B.

In block 422, the device 102 captures a position of the registration tool 108 (e.g., the pointer 112) when the surgeon contacts the registration tool 108 on the patient's bone or on soft tissue covering a portion of the patient's bone. This capture process may be similar to the capture process performed during registration as described above in connection with block 402. In some embodiments, the device 102 may capture and process the position of the registration tool 108 in real time as the surgeon manipulates the tool 108. For example, the surgeon may contact the pointer 112 on cartilage, menisci, or other soft tissue covering the patient's bone at a particular bony landmark. That bony landmark may have been one of the bony landmarks specified for registration as described above in connection with block 402. Additionally, as described above, the captured position may be represented by coordinates in the surgical coordinate system relative to the patient's bone.

In some embodiments, block 422 (like block 402) may involve the device 102 capturing a position at a location on the patient's bony anatomy that is known to have no soft tissue or a small amount of soft tissue. For example, the device 102 may capture positions on the acromion on the patient's scapula. Such captured positions of locations with no soft tissue or a small amount of soft tissue may be useful for confirming proper registration of the bone model.

In block 424, the device 102 determines the difference between each point position captured in block 422 and a corresponding registered position of the bone model, incorporating the associated estimate of soft tissue thickness (including any adjustments to that value made in block 412). For example, the device 102 may determine a distance, in the surgical coordinate system, between the point position captured in block 422 and a corresponding point that is either on the surface of the bone model (where the estimated soft tissue thickness value for that point was zero) or extended from the surface of the bone model by the associated soft tissue thickness (where the value was non-zero). That distance may be a shortest distance, an orthogonal distance, a distance in a predetermined direction, a height, or other measure of distance between the captured point position and the point in the surgical coordinate system represented by the bone model extended by the estimated soft tissue thickness. In that example, a smaller difference indicates that the position of the pointer 112 has a better match to the registered position of the bone model, accounting for estimated soft tissue, at that location. In other words, if the estimated soft tissue thickness matches the actual soft tissue thickness at that location, then the difference between the point position captured in block 422 and a corresponding point on the surface of the registered bone model plus the estimated soft tissue thickness will be zero or close to zero, indicating a good match between the registered bone model and the patient's actual bone.

In block 426, the device 102 displays the difference determined in block 424 to the surgeon and/or another user. The device 102 may display this difference numerically, graphically, or using any other technique. For example, the device 102 may display a distance determined in block 424 as a length in millimeters. As another example, the device 102 may graphically display the bone model along with one or more points, point clouds, surfaces, or other representations of the captured positions. In some embodiments, each point may be color-coded or otherwise marked to indicate a difference between the captured positions and the corresponding registered position of the bone model. For example, a point may be displayed in green when that difference is less than a first threshold (e.g., 0.7 mm, 1 mm, 2 mm, or a different threshold), yellow when that difference is greater than or equal to the first threshold and less than a second threshold (e.g., 1.4 mm, 2 mm, 3 mm, or a different threshold), and red when that difference is greater than or equal to the second threshold. The particular thresholds used for color-coding may be adjusted based on the estimated soft tissue thickness. As such, the device 102 may provide a "green" indication to indicate that the bone model registration is appropriate even when the pointer 112 touches soft tissue at a relatively large distance from the registered bone model surface (e.g., several millimeters).

In block 428, the device 102 determines whether additional locations remain for confirming the registration. The device 102 may verify registration for multiple predetermined landmarks associated with the particular surgical procedure, as described above. If additional locations remain, the method 400 loops back to block 422. If no additional locations remain for confirming the registration, the method 400 advances to block 430, in which the method 400 is completed. The surgical procedure may continue as described above in connection with FIG. 2. In some embodiments, the surgeon may determine to repeat registration, for example if interactive confirmation of the results is unsatisfactory. In those embodiments, the surgeon may repeat automatic registration as described in connection with FIGS. 4A and 4B and/or may perform surgeon-driven registration as described above in connection with FIGS. 3A-3C.

Figure 5:
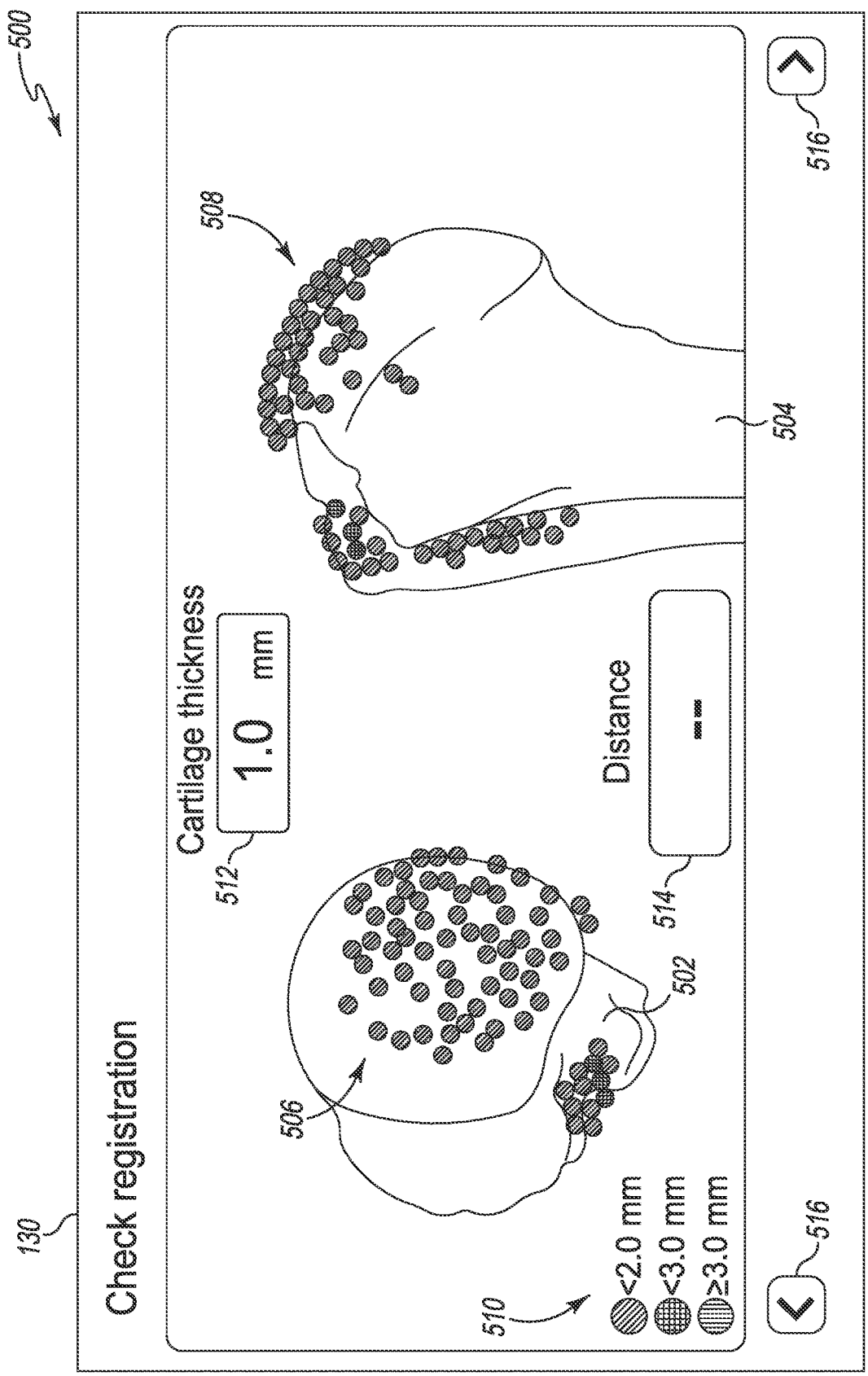
FIGS. 5-10 are schematic diagrams illustrating potential embodiments of a user interface for bone model registration that may be provided by the surgical planning and assistance device of FIG. 1 in connection with the methods of FIGS. 2-4B during the performance of various orthopaedic surgical procedures.

Referring now to FIG. 5, an illustrative embodiment of a user interface 500 that may be provided by the device 102 is shown. In particular, the interface 500 may be a graphical user interface for confirming registration of a bone model, as described above in connection with FIGS. 3A-3C and/or 4A-4B. The user interface 500 may be displayed in connection with registration of a bone model for a humerus, for example during a TSA surgical operation. The user interface 500 includes graphical representations 502, 504 of the bone model of the humerus. The user interface further includes point representations 506, 508 corresponding to captured positions of the pointer 112. Each of those point representations 506, 508 is displayed relative to the registered bone model 502, 504 such that the surgeon may visually confirm registration of the bone model. Additionally, each of the point representations 506, 508 is patterned according to legend 510 to indicate the distance between the captured position and the corresponding point of the registered bone model. As described above, the particular thresholds defined in the legend 510 may be adjusted by the estimated soft tissue thickness. Thus, as shown in FIG. 5, certain points 506, 508 that are displayed as being spaced apart from the surface of the bone models 502, 504 in the user interface 500 are indicated as being correctly registered based on the estimated soft tissue thickness associated with each of those points. The user interface 500 further includes a label 512 that displays soft tissue thickness as a numerical value as well as a label 514 that displays the distance between a captured point and the bone model as a numerical value. The device 102 may update one or more of those labels 512, 514, for example in response to capturing additional positions of the pointer 112. Illustratively, the user interface 500 includes navigation controls 516 that may be used by the surgeon to select a different bony landmark or other location to verify registration of the bone model.

Figure 6:
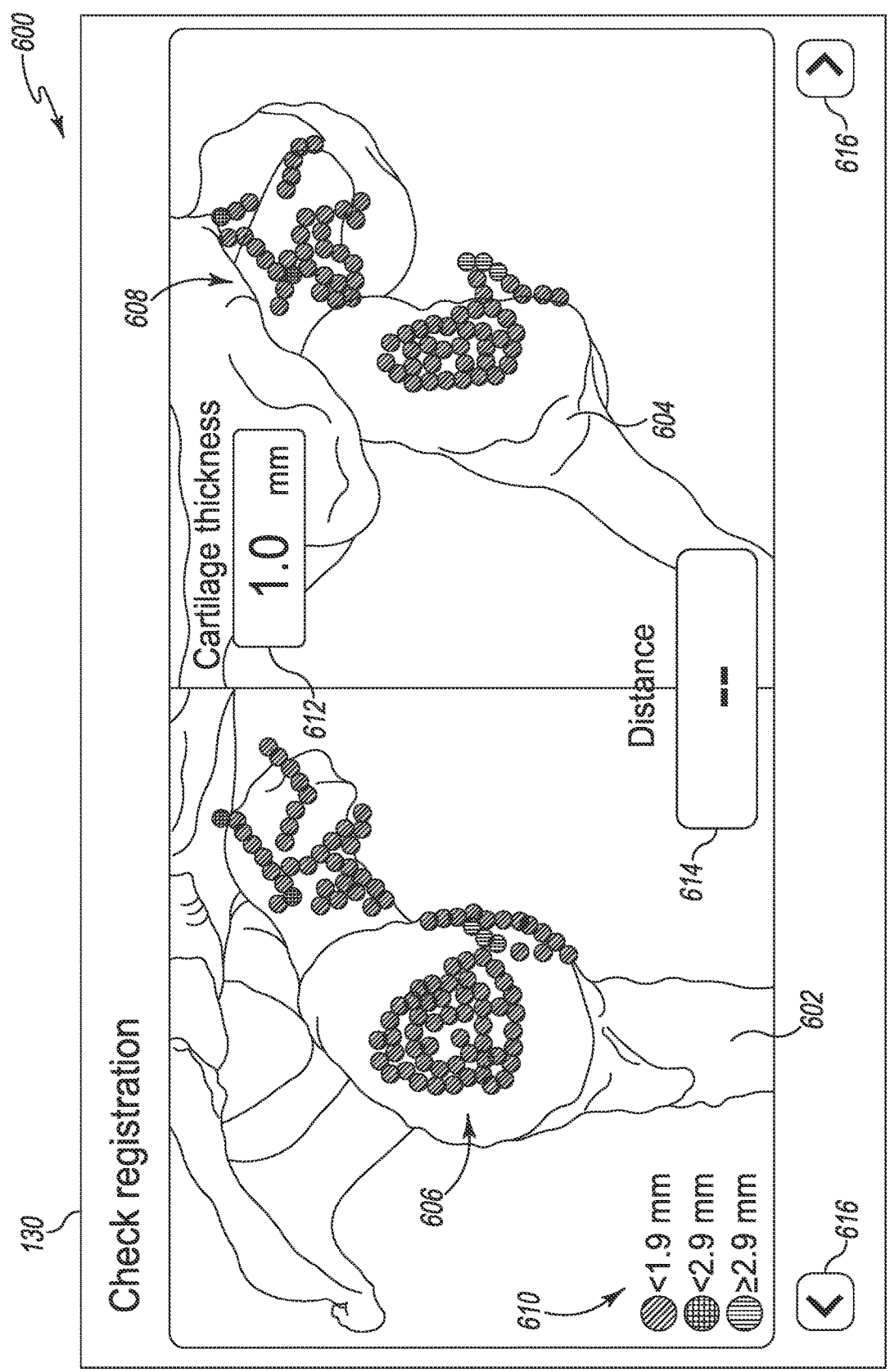

Referring now to FIG. 6, an illustrative embodiment of a user interface 600 that may be provided by the device 102 is shown. In particular, the interface 600 may be a graphical user interface for confirming registration of the bone model as described above in connection with FIGS. 3A-3C and/or 4A-4B. The user interface 600 may be displayed in connection with registration of a bone model for a scapula and shoulder joint, for example during a TSA surgical operation. The user interface 600 includes graphical representations 602, 604 of the bone model of the scapula. The user interface further includes point representations 606, 608 corresponding to captured positions of the pointer 112. Each of those point representations 606, 608 is displayed relative to the registered bone model 602, 604 such that the surgeon may visually confirm registration of the bone model. Additionally, each of the point representations 606, 608 is patterned according to legend 610 to indicate the distance between the captured position and the corresponding point of the registered bone model. As described above, the particular thresholds defined in the legend 610 may be adjusted by the estimated soft tissue thickness. Thus, as shown in FIG. 6, certain points 606, 608 that are displayed as being spaced apart from the surface of the bone models 602, 604 in the user interface 600 are indicated as being correctly registered based on the estimated soft tissue thickness associated with each of those points. The user interface 600 further includes a label 612 that displays soft tissue thickness as a numerical value as well as a label 614 that displays the distance between a captured point and the bone model as a numerical value. The device 102 may update one or more of those labels 612, 614, for example in response to capturing additional positions of the pointer 112. Illustratively, the user interface 600 includes navigation controls 616 that may be used by the surgeon to select a different bony landmark or other location to verify registration of the bone model.

Figure 7:
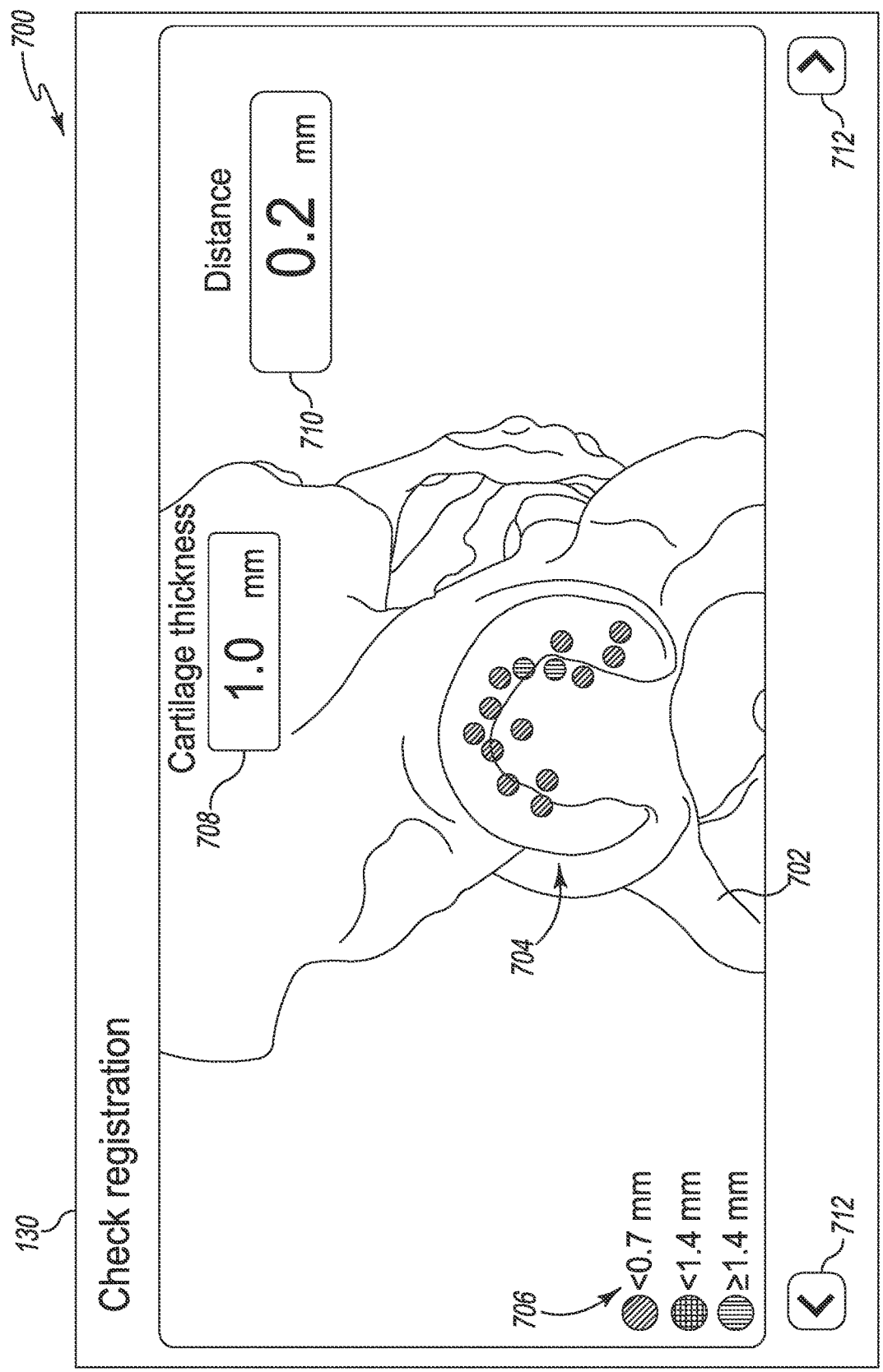

Referring now to FIG. 7, an illustrative embodiment of a user interface 700 that may be provided by the device 102 is shown. In particular, the interface 700 may be a graphical user interface for confirming registration of the bone model as described above in connection with FIGS. 3A-3C and/or 4A-4B. The user interface 700 may be displayed in connection with registration of a bone model for a pelvis including acetabulum, for example during a THA surgical operation. The user interface 700 includes a graphical representation 702 of the bone model of the pelvis. The user interface further includes point representations 704 corresponding to captured positions of the pointer 112. Each of those point representations 704 is displayed relative to the registered bone model 702 such that the surgeon may visually confirm registration of the bone model. Additionally, each of the point representations 704 is patterned according to legend 706 to indicate the distance between the captured position and the corresponding point of the registered bone model. As described above, the particular thresholds defined in the legend 706 may be adjusted by the estimated soft tissue thickness. Thus, as shown in FIG. 7, certain points 704 that are displayed as being spaced apart from the surface of the bone model 702 in the user interface 700 are indicated as being correctly registered based on the estimated soft tissue thickness associated with each of those points. The user interface 700 further includes a label 708 that displays soft tissue thickness as a numerical value as well as a label 710 that displays the distance between a captured point and the bone model as a numerical value. The device 102 may update one or more of those labels 708, 710, for example in response to capturing additional positions of the pointer 112. Illustratively, the user interface 700 includes navigation controls 712 that may be used by the surgeon to select a different bony landmark or other location to verify registration of the bone model.

Figure 8:
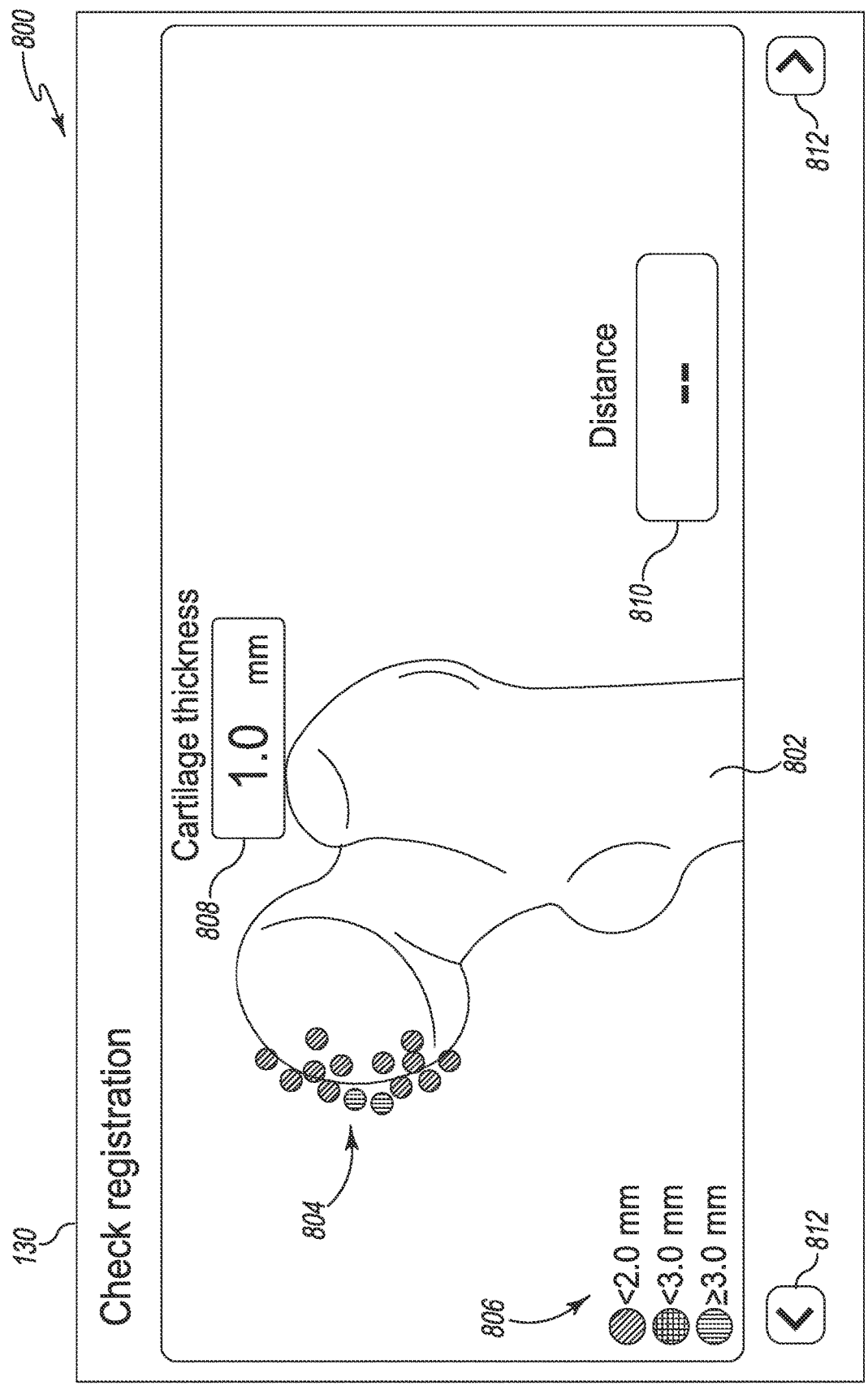

Referring now to FIG. 8, an illustrative embodiment of a user interface 800 that may be provided by the device 102 is shown. In particular, the interface 800 may be a graphical user interface for confirming registration of the bone model as described above in connection with FIGS. 3A-3C and/or 4A-4B. The user interface 800 may be displayed in connection with registration of a bone model for a femur including the femoral head, for example during a THA surgical operation. The user interface 800 includes a graphical representation 802 of the bone model of the femur. The user interface further includes point representations 804 corresponding to captured positions of the pointer 112. Each of those point representations 804 is displayed relative to the registered bone model 802 such that the surgeon may visually confirm registration of the bone model. Additionally, each of the point representations 804 is patterned according to legend 806 to indicate the distance between the captured position and the corresponding point of the registered bone model. As described above, the particular thresholds defined in the legend 806 may be adjusted by the estimated soft tissue thickness. Thus, as shown in FIG. 8, certain points 804 that are displayed as being spaced apart from the surface of the bone model 802 in the user interface 800 are indicated as being correctly registered based on the estimated soft tissue thickness associated with each of those points. The user interface 800 further includes a label 808 that displays soft tissue thickness as a numerical value as well as a label 810 that displays the distance between a captured point and the bone model as a numerical value. The device 102 may update one or more of those labels 808, 810, for example in response to capturing additional positions of the pointer 112. Illustratively, the user interface 800 includes navigation controls 812 that may be used by the surgeon to select a different bony landmark or other location to verify registration of the bone model.

Figure 9:
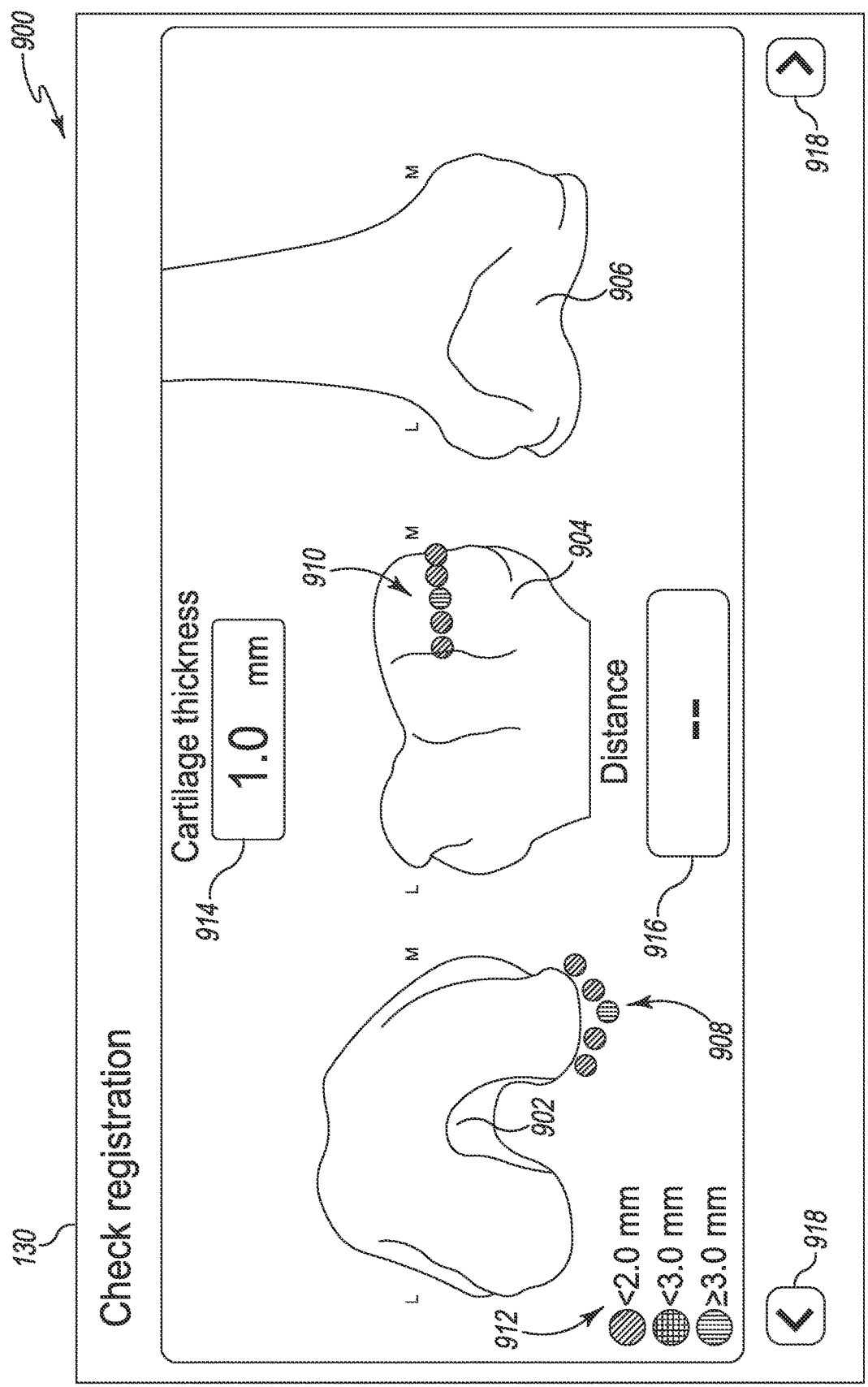

Referring now to FIG. 9, an illustrative embodiment of a user interface 900 that may be provided by the device 102 is shown. In particular, the interface 900 may be a graphical user interface for confirming registration of the bone model as described above in connection with FIGS. 3A-3C and/or 4A-4B. The user interface 900 may be displayed in connection with registration of a bone model for a femur including the distal end of the femur, for example during a TKA surgical operation. The user interface 900 includes graphical representations 902, 904, 906 of the bone model of the femur. The user interface further includes point representations 908, 910 corresponding to captured positions of the pointer 112. Each of those point representations 908, 910 is displayed relative to the registered bone model 902, 904, 906 such that the surgeon may visually confirm registration of the bone model. Additionally, each of the point representations 908, 910 is patterned according to legend 912 to indicate the distance between the captured position and the corresponding point of the registered bone model. As described above, the particular thresholds defined in the legend 912 may be adjusted by the estimated soft tissue thickness. Thus, as shown in FIG. 9, certain points 908, 910 that are displayed as being spaced apart from the surface of the bone models 902, 904, 906 in the user interface 900 are indicated as being correctly registered based on the estimated soft tissue thickness associated with each of those points. The user interface 900 further includes a label 914 that displays soft tissue thickness as a numerical value as well as a label 916 that displays the distance between a captured point and the bone model as a numerical value. The device 102 may update one or more of those labels 914, 916, for example in response to capturing additional positions of the pointer 112. Illustratively, the user interface 900 includes navigation controls 918 that may be used by the surgeon to select a different bony landmark or other location to verify registration of the bone model.

Figure 10:
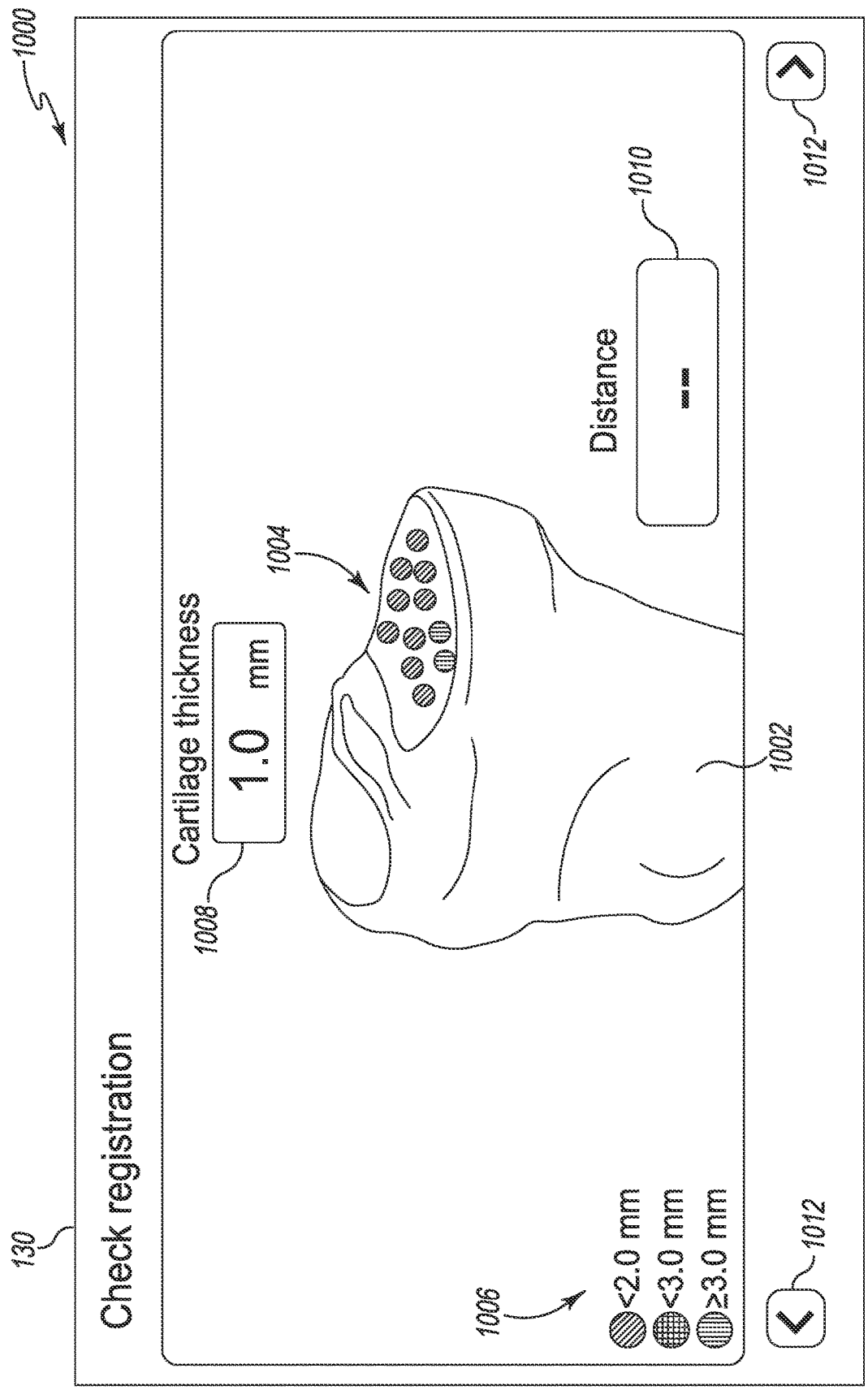

Referring now to FIG. 10, an illustrative embodiment of a user interface 1000 that may be provided by the device 102 is shown. In particular, the interface 1000 may be a graphical user interface for confirming registration of the bone model as described above in connection with FIGS. 3A-3C and/or 4A-4B. The user interface 1000 may be displayed in connection with registration of a bone model for a tibia including the proximal end of the tibia, for example during a TKA surgical operation. The user interface 1000 includes graphical representation 1002 of the bone model of the tibia. The user interface further includes point representations 1004 corresponding to positions of the pointer 112 captured while the surgeon confirms registration of the bone model. Each of those point representations 1004 is displayed relative to the registered bone model 1002 such that the surgeon may visually confirm registration of the bone model. Additionally, each of the point representations 1004 is patterned according to legend 1006 to indicate the distance between the captured position and the corresponding point of the registered bone model. As described above, the particular thresholds defined in the legend 1006 may be adjusted by the estimated soft tissue thickness. Thus, as shown in FIG. 10, certain points 1004 that are displayed as being spaced apart from the surface of the bone model 1002 in the user interface 1000 are indicated as being correctly registered based on the estimated soft tissue thickness associated with each of those points. The user interface 1000 further includes a label 1008 that displays soft tissue thickness as a numerical value as well as a label 1010 that displays the distance between a captured point and the bone model as a numerical value. The device 102 may update one or more of those labels 1008, 1010, for example in response to capturing additional positions of the pointer 112. Illustratively, the user interface 1000 includes navigation controls 1012 that may be used by the surgeon to select a different bony landmark or other location to verify registration of the bone model.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:
1. A bone model registration method comprising:
defining, by a computing device, a surgical coordinate system relative to a bone of a patient;
capturing, by the computing device, a plurality of point positions in the surgical coordinate system, wherein each of the plurality of point positions is associated with an anatomical landmark of the patient's bone, and wherein the plurality of point positions comprises a first point position representing a location on a soft tissue surface covering a portion of the patient's bone;
identifying, by the computing device, for each of the plurality of point positions, an estimated soft tissue thickness value; and
registering, by the computing device, a three-dimensional model of the patient's bone in the surgical coordinate system based on the plurality of point positions and the estimated soft tissue thickness values, wherein registering the three-dimensional model comprises determining, for each of the plurality of point positions, a distance between that point position and a corresponding point from the three-dimensional model extended by the estimated soft tissue thickness value associated with that point position, to determine a set of distances associated with a transformation of the three-dimensional model.
2. The method of claim 1, wherein capturing the plurality of point positions comprises tracking a location of a registration tool having a pointer using a camera array coupled to the computing device, wherein the pointer of the registration tool directly contacts the soft tissue surface but does not directly contact the patient's bone while the first point position is captured.
3. The method of claim 2, wherein the plurality of point positions further comprises a second point position captured while the pointer of the registration tool directly contacts the patient's bone.
4. The method of claim 3, wherein identifying an estimated soft tissue thickness value for each of the plurality of point positions comprises:
identifying the estimated soft tissue thickness value for the first point position as a number greater than zero; and
identifying the estimated soft tissue thickness value for the second point position as zero.
5. The method of claim 2, wherein capturing the plurality of point positions comprises moving the pointer of the registration tool along a surface of the patient's bone or along the soft tissue surface to capture a point cloud associated with an anatomical landmark.
6. The method of claim 1, wherein identifying an estimated soft tissue thickness value for each of the plurality of point positions comprises receiving one or more estimates of soft tissue thickness from a surgeon during an orthopaedic surgical procedure.
7. The method of claim 1, wherein identifying an estimated soft tissue thickness value for each of the plurality of point positions comprises retrieving, from a memory device, one or more initial estimated soft tissue thickness values associated with the plurality of point positions.
8. The method of claim 1, further comprising:
receiving, by the computing device, an updated estimated soft tissue thickness value for at least one of the plurality of point positions; and
re-registering, by the computing device, the three-dimensional model of the patient's bone in the surgical coordinate system based on the plurality of point positions and the estimated soft tissue thickness values, including the at least one updated estimated soft tissue thickness value.
9. The method of claim 1, wherein registering the three-dimensional model further comprises optimizing the set of distances by iteratively adjusting the transformation of the three-dimensional model to improve registration quality of the three-dimensional model.
10. The method of claim 9, wherein registering the three-dimensional model further comprises optimizing the set of distances by iteratively adjusting the estimated soft tissue thickness values associated with one or more of the plurality of point positions to improve registration quality of the three-dimensional model.
11. The method of claim 1, further comprising displaying, by the computing device, after registering the three-dimensional model, a representation of the three-dimensional model in the surgical coordinate system.
12. The method of claim 11, further comprising displaying, by the computing device, the plurality of point positions relative to the displayed representation of the three-dimensional model.
13. The method of claim 12, wherein displaying the plurality of point positions relative to the displayed representation of the three-dimensional model comprises color-coding each of the plurality of point positions as a function of a distance between each point position and a corresponding point from the three-dimensional model extended by the estimated soft tissue thickness value associated with that point position.
14. The method of claim 11, further comprising, after registering the three-dimensional model:
capturing, by the computing device, a confirmation point position while a pointer of a registration tool contacts the soft tissue surface covering the portion of the patient's bone;
displaying, by the computing device, the confirmation point position relative to the displayed representation of the three-dimensional model; and
displaying, by the computing device, a difference between the confirmation point position and a corresponding point from the three-dimensional model extended by the estimated soft tissue thickness value associated with the corresponding point.
15. The method of claim 14, wherein displaying the difference between the confirmation point position and the corresponding point from the three-dimensional model extended by the estimated soft tissue thickness value associated with the corresponding point comprises:
displaying the confirmation point position using a first color if the difference is less than a first threshold; and
displaying the confirmation point position using a second color if the difference is greater than the first threshold, the second color being different from the first color.
16. The method of claim 1, further comprising creating, by the computing device, the three-dimensional model based on one or more preoperative medical images.
17. The method of claim 1, further comprising controlling, by the computing device, a robotic surgical device in the surgical coordinate system based on the three-dimensional model after registering the three-dimensional model.
18. An orthopaedic surgical system comprising:
a computing device configured to:
define a surgical coordinate system relative to a bone of the patient;
capture a plurality of point positions in the surgical coordinate system, wherein each of the plurality of point positions is associated with an anatomical landmark of the patient's bone, and wherein the plurality of point positions comprises a first point position representing a location on a soft tissue surface covering a portion of the patient's bone;

identify, for each of the plurality of point positions, an estimated soft tissue thickness value; and register a three-dimensional model of the patient's bone in the surgical coordinate system based on the plurality of point positions and the estimated soft tissue thickness values at least in part by determining, for each of the plurality of point positions, a distance between that point position and a corresponding point from the three-dimensional model extended by the estimated soft tissue thickness value associated with that point position, to determine a set of distances associated with a transformation of the three-dimensional model.

19. The system of claim 18, further comprising:
a registration tool having a pointer configured to be contacted with various locations on a patient's anatomy; and
a camera array coupled to the computing device;
wherein the computing device is configured to capture the plurality of point positions by tracking a location of the registration tool using the camera array, and wherein the computing device is configured to capture the first point position while the pointer of the registration tool directly contacts the soft tissue surface but does not directly contact the patient's bone.

20. The system of claim 18, further comprising a robotic surgical device configured to assist with resection of the patient's bone, wherein the computing device is further configured to control the robotic surgical device in the surgical coordinate system based on the three-dimensional model after registering the three-dimensional model.

* * * * *